(12) United States Patent
Shim et al.

(10) Patent No.: US 9,795,309 B2
(45) Date of Patent: Oct. 24, 2017

(54) WEARABLE MOBILE TERMINAL

(71) Applicant: LG ELECTRONICS INC., Seoul (KR)

(72) Inventors: Hongjo Shim, Seoul (KR); Gukchan Lim, Seoul (KR); Youngho Sohn, Seoul (KR); Seonghyok Kim, Seoul (KR); Hyunwoo Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 21 days.

(21) Appl. No.: 14/640,957

(22) Filed: Mar. 6, 2015

(65) Prior Publication Data
US 2015/0359436 A1    Dec. 17, 2015

(30) Foreign Application Priority Data

Jun. 11, 2014  (KR) .................. 10-2014-0070881

(51) Int. Cl.
*A61B 5/024* (2006.01)
*A61B 5/00* (2006.01)

(52) U.S. Cl.
CPC .......... *A61B 5/02427* (2013.01); *A61B 5/486* (2013.01); *A61B 5/4866* (2013.01); *A61B 5/681* (2013.01); *A61B 5/721* (2013.01); *A61B 5/7221* (2013.01); *A61B 5/7246* (2013.01); *A61B 5/7278* (2013.01); *A61B 5/743* (2013.01); *A61B 2562/0219* (2013.01)

(58) Field of Classification Search
CPC ... A61B 5/02427; A61B 5/486; A61B 5/4866; A61B 5/681; A61B 5/721
See application file for complete search history.

(56) References Cited

U.S. PATENT DOCUMENTS 7,468,036 B1 * 12/2008 Rulkov .............. A61B 5/02438
600/485
2002/0109600 A1 * 8/2002 Mault .................. A61B 5/1112
340/573.1

* cited by examiner

*Primary Examiner* — Joseph Dietrich
(74) *Attorney, Agent, or Firm* — Lee, Hong, Degerman, Kang & Waimey

(57) ABSTRACT

A wearable terminal can include a main body configured to be in contact with a body of a user using one side of the main body, a photo plethysmography including a transmitter combined with one side of the main body and outputs a output signal, and a receiver detecting a reflection signal corresponding to the output signal returned, a cover configured to cover the photo plethysmography and be combined with the main body and a controller configured to measure a heart rate based on a reflection signal measured by the photo plethysmography. The cover is combined with the main body and parts corresponding to the transmitter and the receiver of the photo plethysmography include transparent units through which the output signal and the reflection signal are passing and a barrier unit positioned between the transparent units and shielding the output signal and the reflection signal.

19 Claims, 31 Drawing Sheets

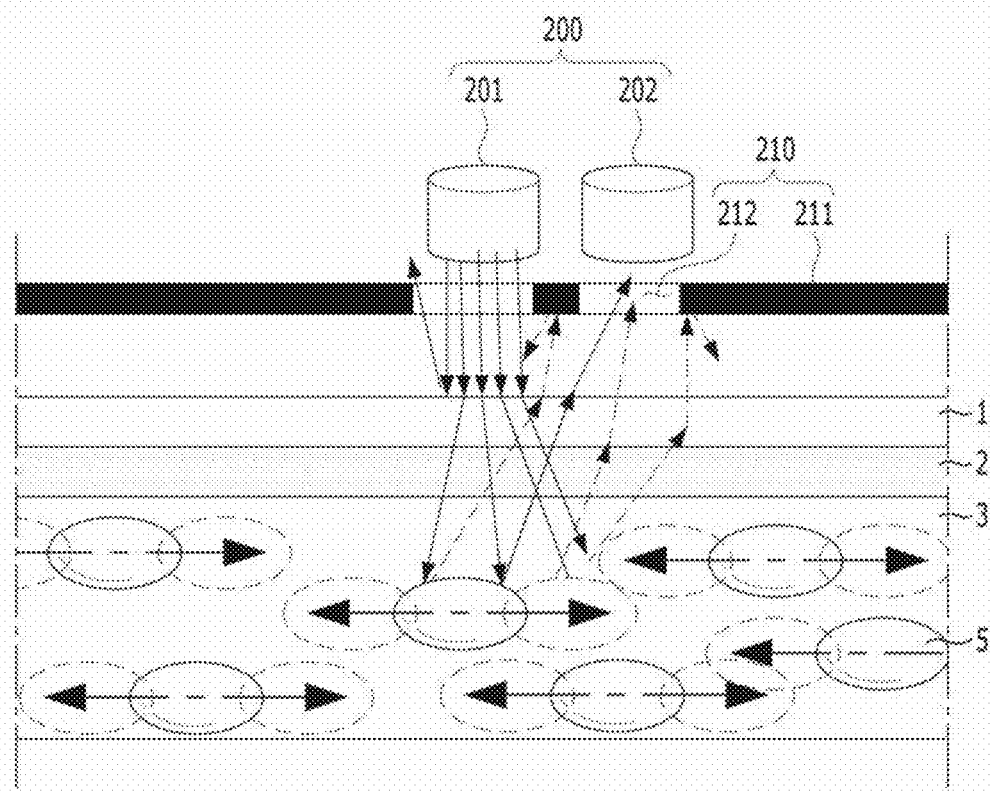

WEARABLE MOBILE TERMINAL

Pursuant to 35 U.S.C. §119(a), this application claims the benefit of earlier filing date and right of priority to Korean Patent Application No. 10-2014-0070881 filed on Jun. 11, 2014, the contents of which are all hereby incorporated by reference herein in their entirety.

BACKGROUND OF THE INVENTION

Field of the Invention

The present invention relates to a mobile terminal capable of minimizing an error caused by a movement of a user in case of measuring a pulse wave using a PPG (photo plethysmography).

Discussion of the Related Art

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

As functions of a terminal are diversifying, the terminal is implemented as a form of a multimedia player equipped with such complex functions as capturing a picture or a video, playing music or a video file, gaming, broadcast reception and the like.

Efforts are ongoing to support and increase the functionality of mobile terminals. Such efforts include software and hardware improvements, as well as changes and improvements in the structural components.

In order for a user easily carry a mobile terminal all the time, a wearable mobile terminal capable of being worn on a user like accessories such as a mobile terminal of a watch type worn on a wrist, a mobile terminal of a glasses type capable of being worn on a user like a glasses and the like is emerging.

Since a wearable mobile terminal maintains a state of being worn on a body of a user all the time, the wearable mobile terminal can consistently monitor a change of the body. Hence, the wearable mobile terminal can collect data by measuring changes of a body temperature, a heart rate and the like.

SUMMARY OF THE INVENTION

An object of the present invention is to provide a mobile terminal capable of minimizing an error caused by a movement of a user in case of measuring a pulse wave using a PPG (photo plethysmography).

To achieve these objects and other advantages and in accordance with the purpose of the invention, as embodied and broadly described herein, a wearable terminal includes a main body configured to be in contact with a body of a user using one side of the main body, a photo plethysmography configured to include a transmitter, which is combined with one side of the main body and outputs a output signal, and a receiver detecting a reflection signal corresponding to the output signal returned in a manner of being reflected, a cover configured to cover the photo plethysmography and be combined with the main body and a controller configured to measure a heart rate based on a reflection signal measured by the photo plethysmography. The cover is combined with the main body and parts corresponding to the transmitter and the receiver of the photo plethysmography include transparent units through which the output signal and the reflection signal are passing and a barrier unit positioned between the transparent units and shielding the output signal and the reflection signal.

The wearable terminal can further include a rubber, which is positioned between the cover and the photo plethysmography and includes an opening formed on a part corresponding to the transparent units.

The cover and the main body can be combined with each other by a waterproof tape.

The transmitter of the photo plethysmography may use a green LED configured to output a green light.

A wearable terminal includes a main body configured to be in contact with a body of a user using one side of the main body, a photo plethysmography configured to include a transmitter, which is combined with one side of the main body and outputs a output signal, and a receiver detecting a reflection signal corresponding to the output signal returned in a manner of being reflected in a blood cell in a blood vessel of the user, an acceleration sensor configured to detect a movement of the main body and a controller configured to calculate a reflection signal data based on a direction and a speed of the movement detected by the acceleration sensor in a manner of compensating a reflection signal detected by the photo plethysmography, the controller configured to calculate a heart rate based on the number of changes of the reflection signal data per reference time.

If the movement of the main body is detected by the acceleration sensor with a prescribed cycle, the controller can eliminate a change of the reflection signal with an interval corresponding to the prescribed cycle.

If the movement of the main body moving in a direction opposite to a direction of the main body is detected by the acceleration sensor, the controller can amplify a size of a detected reflection signal. If the movement of the main body moving in a direction identical to the direction of the main body is detected by the acceleration sensor, the controller can decrease the size of the detected reflection signal.

If a movement moving in a direction opposite to a direction of the main body is detected by the acceleration sensor, the controller can lower the abnormal signal cut-off level of the reflection signal and if a movement moving in a direction identical to the direction of the main body is detected by the acceleration sensor, the controller can raise the abnormal signal cut-off level of the reflection signal.

If a movement moving in a direction opposite to a moving direction of the blood cell is detected by the acceleration sensor, the controller can amplify a measurement value of the reflection signal and if a movement moving in a direction identical to the moving direction of the blood cell is detected by the acceleration sensor, the controller can decrease the measurement value of the reflection signal.

The controller measures a step count of the user using the acceleration sensor and can calculate calorie consumption based on a size of the calculated heart rate and the step count.

The wearable terminal can further include a GPS module configured to transceive location information of the user. The controller can calculate a moving speed of the user in a manner of detecting a location change calculated by the GPS module. If the moving speed is faster than a reference speed, the controller increases the calorie consumption, if the moving speed is slower than the reference speed, the controller can decrease the calorie consumption.

The controller measures a step count and a speed of the user using the acceleration sensor and calculates calorie consumption corresponding to the step count. If a size of the calculated heart rate is greater than a reference heart rate, the controller can increase the calorie consumption. If the size of the calculated heart rate is greater than the reference heart rate, the controller can decrease the calorie consumption.

If a movement moving more than a reference size is detected by the acceleration sensor, the controller can drive the photo plethysmography. If a movement moving less than the reference size is detected by the acceleration sensor, the controller can switch the photo plethysmography into an idle state.

If a size of a movement detected by the acceleration sensor is enlarged, the controller can strengthen strength of a light delivered by the transmitter of the photo plethysmography or make a delivery cycle to be short.

A wearable terminal includes a main body configured to be in contact with a body of a user using one side of the main body, a photo plethysmography configured to include a transmitter, which is combined with one side of the main body and outputs a output signal, and a receiver detecting a reflection signal corresponding to the output signal returned in a manner of being reflected, an acceleration sensor configured to detect a movement of the main body and a controller configured to measure a heart rate based on the reflection signal measured by the photo plethysmography, the controller, if the signal strength measured by the photo plethysmography is out of a range of a valid signal strength, configured to warn the user.

The wearable terminal further includes a display unit positioned at a different side of the main body and a guide screen guiding the user to change a position of the main body can be provided on the display unit.

The guide screen can include a signal indicator, which becomes large when the signal strength measured by the photo plethysmography is strong and becomes small when the signal strength is weak, and a reference indicator, which is positioned in a manner of being separated from the signal indicator in a direction to which the main body should be moved to make the measured signal to be positioned within the range of the valid signal strength.

The wearable terminal can include a confidence level indicator indicating a ratio of the signal strength measured by the photo plethysmography belonging to the range of the valid signal strength.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings, which are given by illustration only, and thus are not limitative of the present invention, and wherein:

FIG. 8 is a diagram for explaining a measuring principle of a photo plethysmography of a wearable terminal shown in FIG. 7;

DETAILED DESCRIPTION OF THE PREFERRED EMBODIMENTS

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Figure 1:
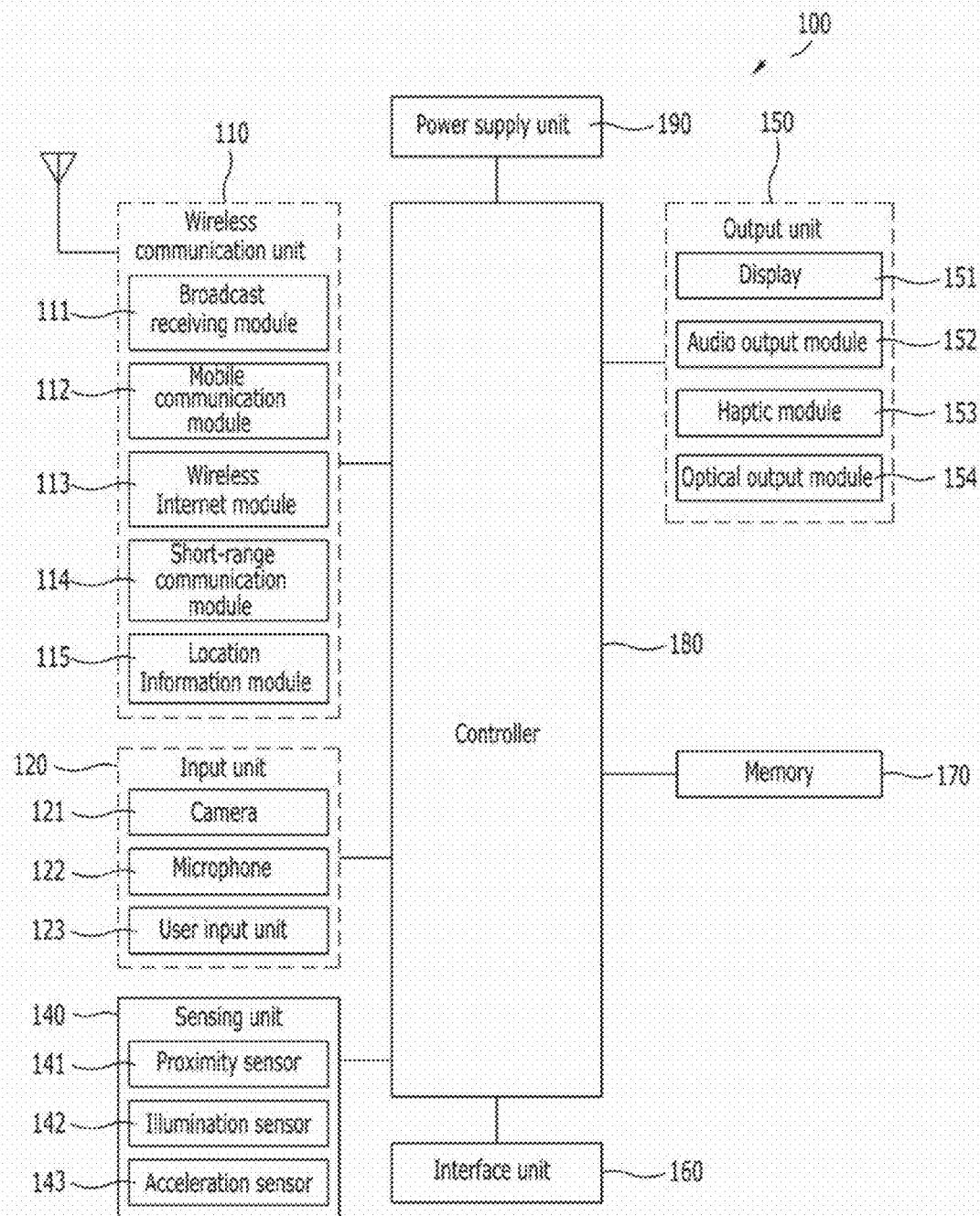
FIG. 1 is a diagram for a configuration of a wearable terminal according to one embodiment of the present invention.
Figure 2:
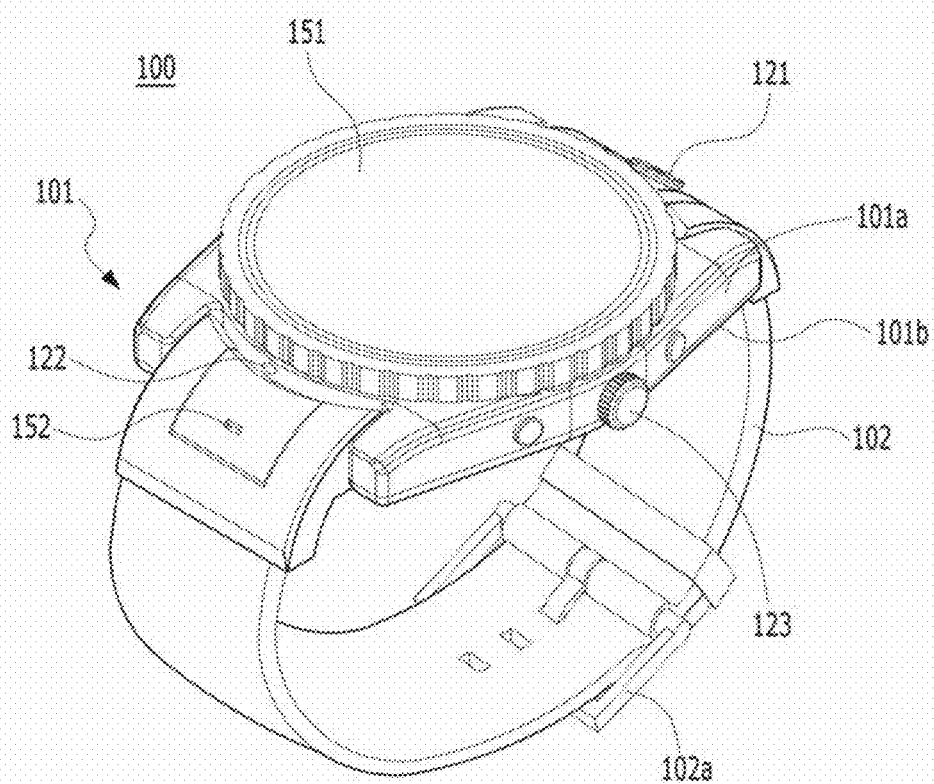
FIG. 2 is a perspective diagram for a wearable terminal according to one embodiment of the present invention.

Reference is now made to FIGS. 1 and 2, where FIG. 1 is a block diagram of a wearable mobile terminal in accordance with the present disclosure, and FIG. 2 is a perspective view illustrating one example of a wearable mobile terminal 100 according to another exemplary embodiment.

The wearable mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

Such devices go beyond the usual technique of a user grasping the wearable mobile terminal using their hand. Examples of the wearable device include a smart watch, a smart glass, a head mounted display (HMD), and the like.

Referring now to FIG. 1A, the wearable mobile terminal 100 is shown having wireless communication unit 110 configured with several commonly implemented components. For instance, the wireless communication unit 110 typically includes one or more components which permit wireless communication between the wearable mobile terminal 100 and a wireless communication system or network within which the wearable mobile terminal is located.

The wireless communication unit 110 typically includes one or more modules which permit communications such as wireless communications between the wearable mobile terminal 100 and a wireless communication system, communications between the wearable mobile terminal 100 and another mobile terminal, communications between the wearable mobile terminal 100 and an external server. Further, the wireless communication unit 110 typically includes one or more modules which connect the wearable mobile terminal 100 to one or more networks.

To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the wearable mobile terminal, the surrounding environment of the wearable mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The wearable mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the wearable mobile terminal 100 and a user, as well as function as the user input unit 123 which provides an input interface between the wearable mobile terminal 100 and the user.

The interface unit 160 serves as an interface with various types of external devices that can be coupled to the wearable mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the wearable mobile terminal 100 may perform assorted control functions associated with a connected external device, in response to the external device being connected to the interface unit 160.

The memory 170 is typically implemented to store data to support various functions or features of the wearable mobile terminal 100. For instance, the memory 170 may be configured to store application programs executed in the wearable mobile terminal 100, data or instructions for operations of the wearable mobile terminal 100, and the like. Some of these application programs may be downloaded from an external server via wireless communication. Other application programs may be installed within the wearable mobile terminal 100 at time of manufacturing or shipping, which is typically the case for basic functions of the wearable mobile terminal 100 (for example, receiving a call, placing a call, receiving a message, sending a message, and the like). It is common for application programs to be stored in the memory 170, installed in the wearable mobile terminal 100, and executed by the controller 180 to perform an operation (or function) for the wearable mobile terminal 100.

The controller 180 typically functions to control overall operation of the wearable mobile terminal 100, in addition to the operations associated with the application programs.

The controller 180 may provide or process information or functions appropriate for a user by processing signals, data, information and the like, which are input or output by the various components depicted in FIG. 1A, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the wearable mobile terminal 100. The power supply unit 190 may include a battery, and the battery may be configured to be embedded in the terminal body, or configured to be detachable from the terminal body.

FIG. 2 is a perspective diagram for a mobile terminal of a watch-type as an example of a wearable mobile terminal 100 related to a different one embodiment of the present invention. Besides the mobile terminal of the watch-type, a wearable terminal 100, which is worn on a user in a state of being contacted to a body of the user, also belongs to the present invention. For clarity of explanation, the present invention is explained on the basis of the wearable terminal 100 of the watch-type in the following description.

As illustrated in FIG. 2, the watch-type mobile terminal 100 includes a main body 101 with a display unit 151 and a band 102 connected to the main body 101 to be The main body 101 may include a case having a certain appearance.

As illustrated, the case may include a first case 101a and a second case 101b cooperatively defining an inner space for accommodating various electronic components. Other configurations are possible. For instance, a single case may alternatively be implemented, with such a case being configured to define the inner space, thereby implementing a wearable mobile terminal 100 with a uni-body.

The wearable mobile terminal 100 can perform wireless communication, and an antenna for the wireless communication can be installed in the main body 101. The antenna may extend its function using the case. For example, a case including a conductive material may be electrically connected to the antenna to extend a ground area or a radiation area.

The display unit 151 is shown located at the front side of the main body 101 so that displayed information is viewable to a user. In some embodiments, the display unit 151 includes a touch sensor so that the display unit can function as a touch screen. As illustrated, window 151a is positioned on the first case 101a to form a front surface of the terminal body together with the first case 101a.

The illustrated embodiment includes audio output module 152, a camera 121, a microphone 122, and a user input unit 123 positioned on the main body 101. When the display unit 151 is implemented as a touch screen, additional function keys may be minimized or eliminated. For example, when the touch screen is implemented, the user input unit 123 may be omitted.

The band 102 is commonly worn on the user's wrist and may be made of a flexible material for facilitating wearing of the device. As one example, the band 102 may be made of fur, rubber, silicon, synthetic resin, or the like. The band 102 may also be configured to be detachable from the main body 101. Accordingly, the band 102 may be replaceable with various types of bands according to a user's preference.

In one configuration, the band 102 may be used for extending the performance of the antenna. For example, the band may include therein a ground extending portion (not shown) electrically connected to the antenna to extend a ground area.

The band 102 may include fastener 102a. The fastener 102a may be implemented into a buckle type, a snap-fit hook structure, a Velcro® type, or the like, and include a flexible section or material. The drawing illustrates an example that the fastener 102a is implemented using a buckle.

Since the wearable terminal 100 according to the present invention is able to maintain a state of being contacted with a body of a user, the wearable terminal can collect such biometric data as a body temperature, a heart rate and the like. Hence, the wearable terminal 100 can include a thermometer or a photo plethysmography (hereinafter abbreviated PPG) 200.

Since the PPG 200 outputs an electromagnetic wave in a state of being adjacent to a body of a user and measures an amount of the reflected and detected electromagnetic wave, the PPG is installed in a direction of a side contacted with the user of the wearable terminal 100. In case of a mobile terminal of the watch-type, the PPG can be installed in a rear side of a main body 101.

The present invention relates to the wearable terminal 100 equipped with the PPG 200. Since a user lives while the wearable terminal 100 is worn on the user, the wearable terminal 100 can consistently obtain data on a heart rate. In case of using an application installed in the wearable terminal 100, a physical condition can be measured using the obtained data on the heart rate and a consumed calorie can be calculated using the data on the heart rate. Various functions can be implemented by utilizing the heart rate data.

Figure 3:
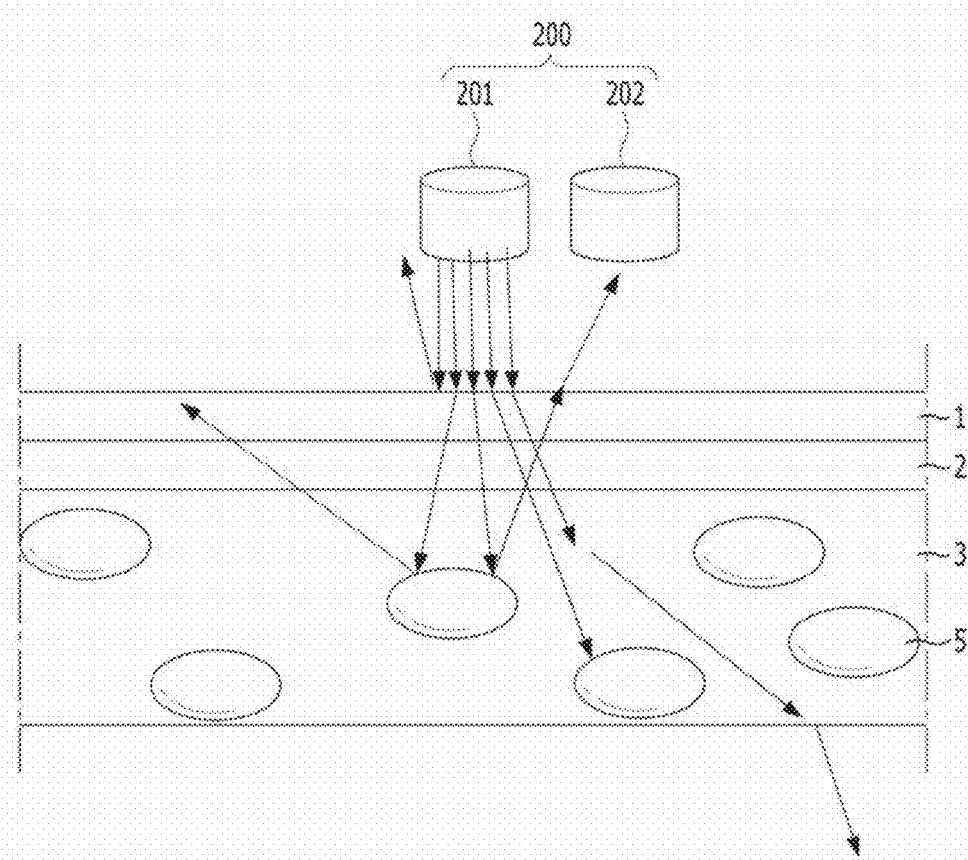
FIG. 3 is a diagram for explaining a principle of a photo plethysmography.

FIG. 3 is a diagram for explaining a principle of a photo plethysmography (PPG) 200. The PPG 200 includes a transmitter 201 configured to transmit an output signal and a receiver 202 configured to detect a reflection signal corresponding to the output signal which is returned in a manner of being reflected.

An output signal corresponds to an electromagnetic wave. For instance, the output signal may have a specific color such as a green color or a blue color. The transmitter 201 can be implemented using a LED. The transmitter 201 can transmit an output signal with a prescribed interval.

An output signal shot from the transmitter 201 passes through skin 1, 2, arrives at a blood vessel 3 and is reflected in a red blood cell 5. A light, which is not arrived at the red blood cell 5, penetrates a body of a user. The receiver 202 is positioned in a manner of being separated from the transmitter 201 and detects a reflection signal of the output signal returning to the PPG 200 by being reflected.

If an amount of red blood cell 5 is large in a blood vessel 3, strength of a reflection signal is strong. On the contrary, if the amount of the red blood cell 5 is small in the blood vessel 3, strength of the reflection signal is weak. Blood in the blood vessel 3 is circulated by power that supplies blood by a heartbeat. The strength of the reflection signal becomes strong when a heart is contracted to push blood out. The strength of the refection signal becomes weak when the heart is relaxed. A heart rate, i.e., heart beat can be measured by measuring a cycle that the strength of the reflection signal becomes strong and weak.

Figure 4:
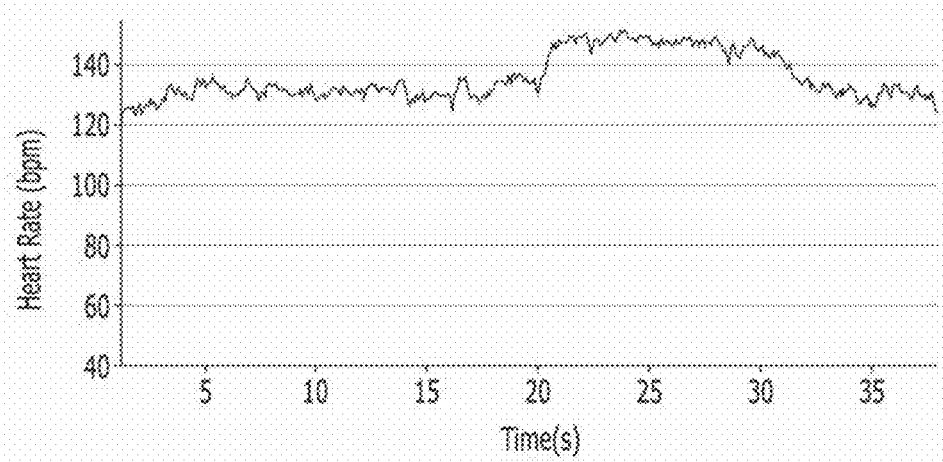
FIG. 4 is a graph showing a measurement result of a photo plethysmography shown in FIG. 3.

FIG. 4 is a graph showing a measurement result of a photo plethysmography 200 shown in FIG. 3. A horizontal axis indicates time and a vertical axis indicates strength of a reflection signal. A graph of a wave form is derived from a heartbeat. When a heartbeat of a user is measured in a stable posture, such a stable wave form as shown in FIG. 4 can be obtained.

Yet, in case that a user moves while wearing a wearable terminal 100, since the wearable terminal 100 is not bonded on a body of the user, the wearable terminal 100 also moves according to the movement of the user. And, a blood cell 5 in a blood vessel 3 is also shaking according to the movement of the user. If a band 102 is tightly fastened, a movement of the wearable terminal may be reduced. Yet, wearing sensation may decrease.

Figure 5:
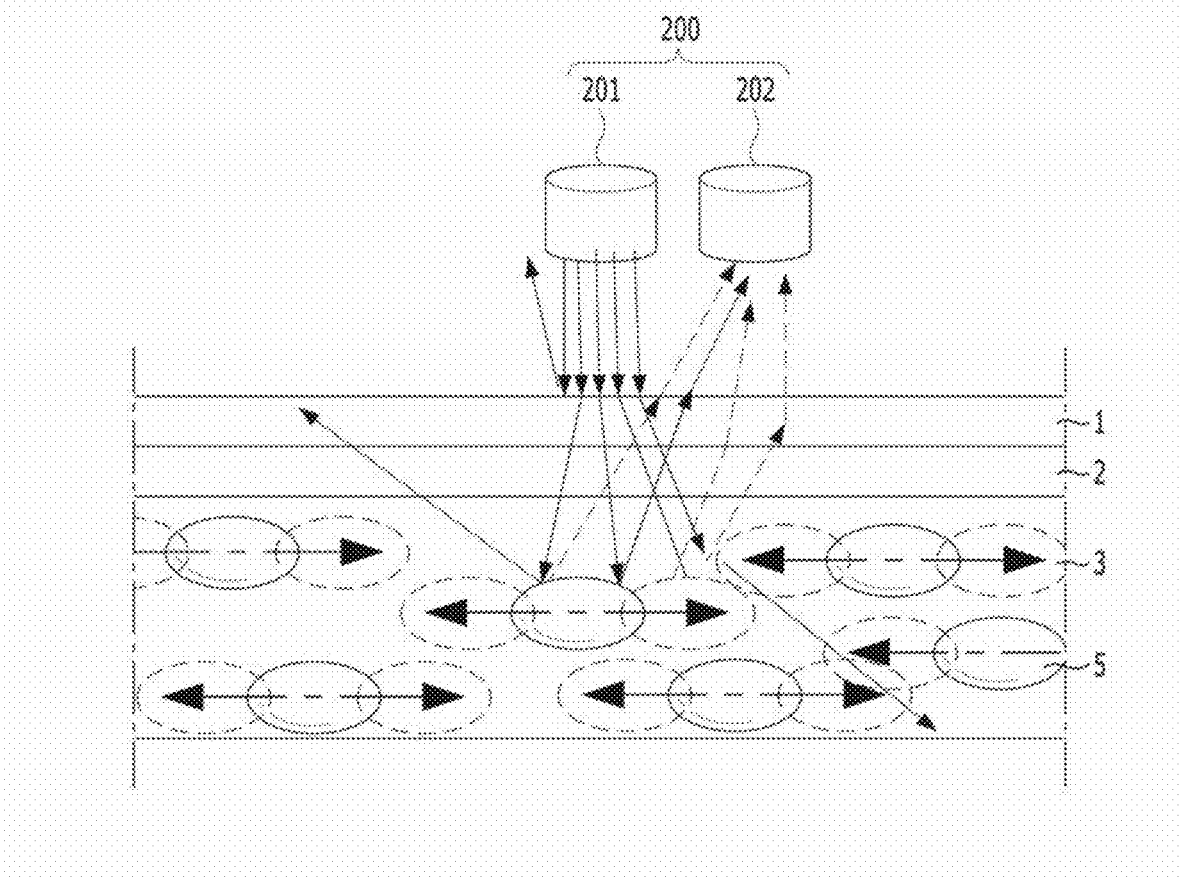
FIG. 5 is a graph showing a measurement result of a legacy photo plethysmography in case that a user is moving.
Figure 6:
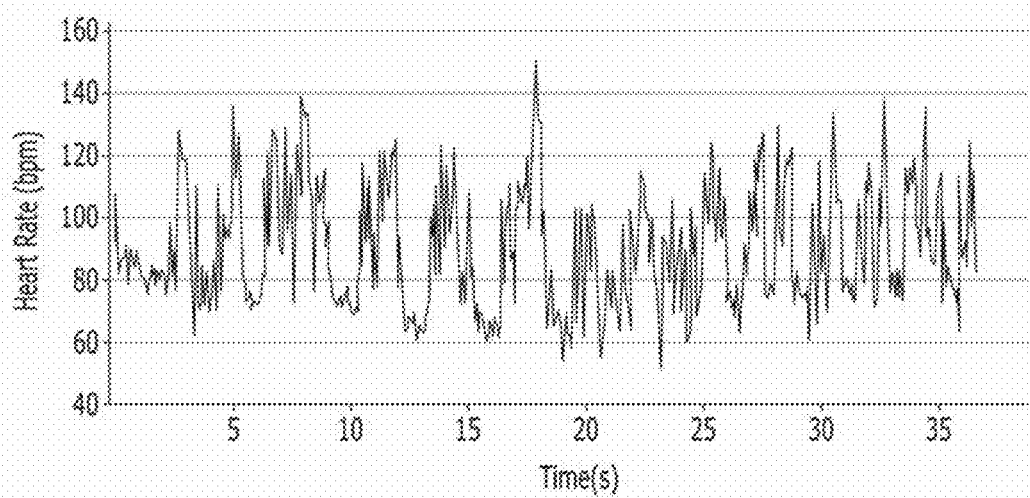
FIG. 6 is a graph showing a measurement result of a photo plethysmography of FIG. 5.

FIG. 5 is a graph showing a measurement result of a legacy photo plethysmography 200 in case that a user is moving and FIG. 6 is a graph showing a measurement result of the photo plethysmography 200 shown in FIG. 5.

As shown in FIG. 5, in case that a user is moving, a blood cell 5 is also moving. Or, according to a movement of a wearable terminal 100, the blood cell 5 is moving on the basis of a photo plethysmography 200. Hence, a lot of reflection signals are detected or an amount of a detected reflection signal may decrease.

Hence, a case of FIG. 5 makes a result of an unstable wave form shown in FIG. 6. In this case, since it is difficult to precisely measure a cycle of increasing and decreasing blood flow amount, it is difficult to precisely measure a heart rate.

If a change of a reflection signal resulted from a movement is detected as a cycle, a heartbeat can be calculated as a big value. Hence, it is required to eliminate the noise.

Figure 7:
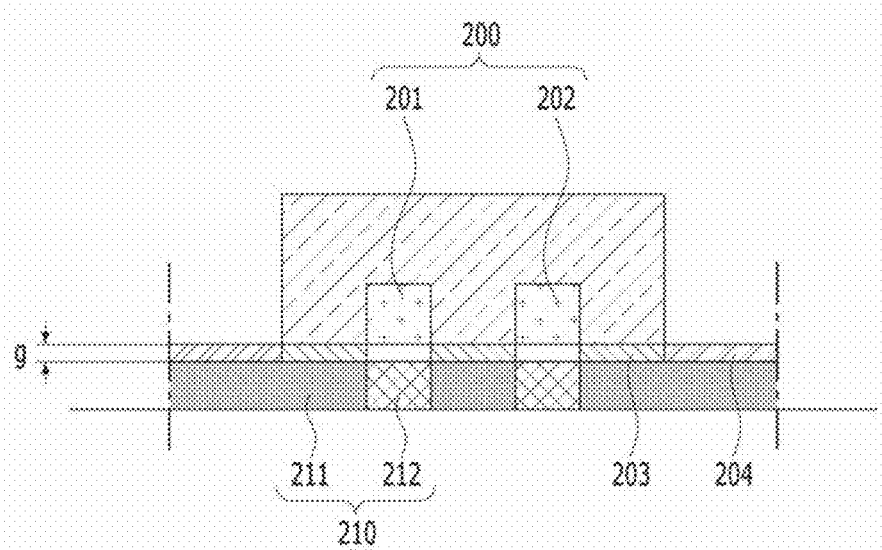
FIG. 7 is a diagram for a cross section of a photo plethysmography of a wearable terminal according to one embodiment of the present invention.

FIG. 7 is a diagram for a cross section of a photo plethysmography 200 of a wearable terminal 100 according to one embodiment of the present invention and FIG. 8 is a diagram for explaining a measuring principle of the photo plethysmography 200 of the wearable terminal 100 shown in FIG. 7.

Referring to FIG. 7, the photo plethysmography 200 is combined with a rear side of a second case 101b of a main body 101 and includes a transmitter 201 and a receiver 202. The photo plethysmography 200 further includes a cover 210 covering the photo plethysmography 200 and protecting the photo plethysmography 200 in a manner of being combined with the rear case 101b. In order to make a output signal shot from the photo plethysmography 200 and a reflection signal returning in a manner of being reflected in a blood cell 5 pass through, the cover 210 can be made up of a material through which signals of a frequency corresponding to the output signal and the reflection signal are able to pass.

In order to reduce a noise of a reflection signal due to a movement of a user, a cover 210 attached to a wearable terminal 100 according to the present invention can further include transparent units 212 making a output signal and a reflection signal penetrate and a barrier unit 211 shielding the output signal and the reflection signal.

As shown in FIG. 7 and FIG. 8, the transparent units 212 are arranged at positions corresponding to the transmitter 201 and the receiver 202 and other parts are configured by the barrier unit 211 to block the noise reflected by movement by the barrier unit 211.

Both sides of the cover 210 are equipped with an adhesive tape 204 to cover the photo plethysmography 200 and combine the cover 210 with a housing. The adhesive tape 204 can prevent water from being flowed in a gap between the cover 210 and the rear case 101b using a waterproof tape.

A gap (g) between the cover 210 and the photo plethysmography 200 can be equipped with a rubber 203 in which an opening is formed at a part corresponding to the transmitter 201 and the receiver 202. The rubber 203 can reduce an error, which is occurred by directly flowing a light shot from the transmitter 201 into the receiver 202, in a manner of shielding a gap between the transmitter 201 and the receiver 202.

And, a noise value occurs in the photo plethysmography 200 can be reduced using an acceleration sensor 143. A method of reducing the noise using the acceleration sensor 143 can be applied to not only a reflection signal data obtained by the photo plethysmography 200 equipped with the cover 210 but also a reflection signal data obtained by the photo plethysmography 200 which is not equipped with the cover 210. Yet, in case of the former case, since a raw data itself corresponds to a data of a state in which noise is eliminated, it is able to obtain more precise reflection signal data.

The acceleration sensor 143 corresponds to a device configured to measure such a dynamic force as acceleration of an object, vibration, impact and the like.

In case of a mechanical acceleration sensor, acceleration is measured using such a resilient member as a spring. Yet, in order to be mounted on a wearable terminal 100 according to the present invention, it is preferable to use an electronic acceleration sensor or a voltage type acceleration sensor. The electronic acceleration sensor measures an amount of movement of a driving part including an appropriate mass by electromotive force of a magnet and a coil. On the contrary, the voltage type acceleration sensor measures acceleration using a piezoelectric element, which generates voltage in case of putting a pressure on the piezoelectric element.

Since acceleration changes when a user is moving, a movement of the user can be detected using the acceleration sensor 143. According to the present invention, the movement of the user is identified using a change of the acceleration detected by the acceleration sensor 143 and noise due to the movement of the user can be eliminated by filtering a reflection signal shot from the photo plethysmography 200 in consideration of the movement.

Figure 9A:
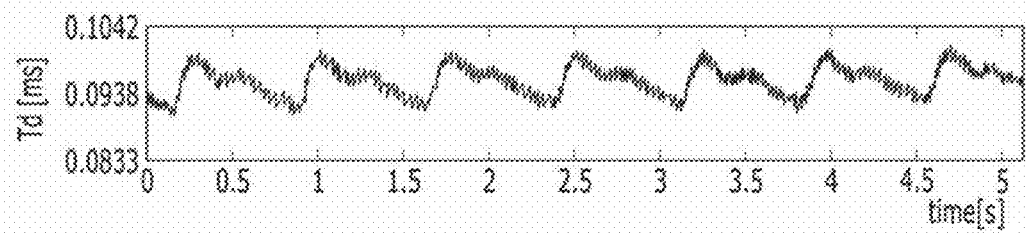
FIGS. 9A and 9B are a graph for a result measured by a photo plethysmography of a legacy wearable terminal.
Figure 9B:
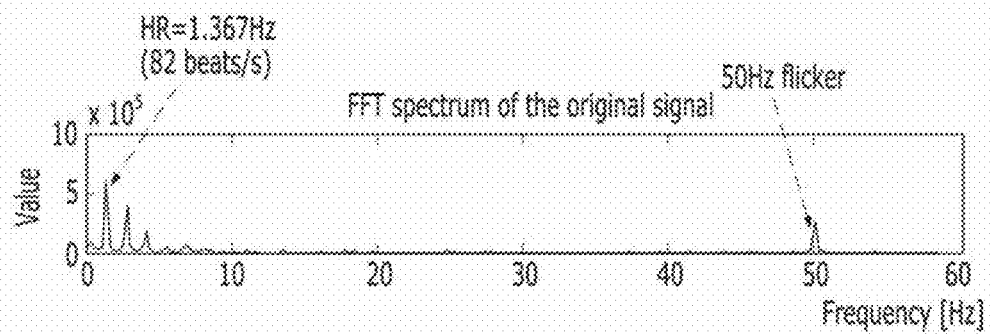

FIG. 9 is a graph for a result measured by a photo plethysmography 200 of a legacy wearable terminal 100.

FIG. 9 A shows a reflection signal raw data measured by the photo plethysmography 200 in case that the wearable terminal is moving. A size of a reflection signal changes with a cycle corresponding to a heartbeat and the size of the reflection signal changes with a short cycle between the cycles corresponding to the heartbeat. If a result of FIG. 9 A including the reflection signal change of the short cycle due to the movement of the wearable terminal is converted into a graph for the cycle using FFT (Fast-Fourier Transform), as shown in FIG. 9 B, a measurement value is indicated on a frequency of 50 Hz. The value corresponds to a noise derived from a minimal change amount. Due to the noise, a frequency value of an actual heart rate corresponding to 1.367 Hz band becomes smaller.

Figure 10A:
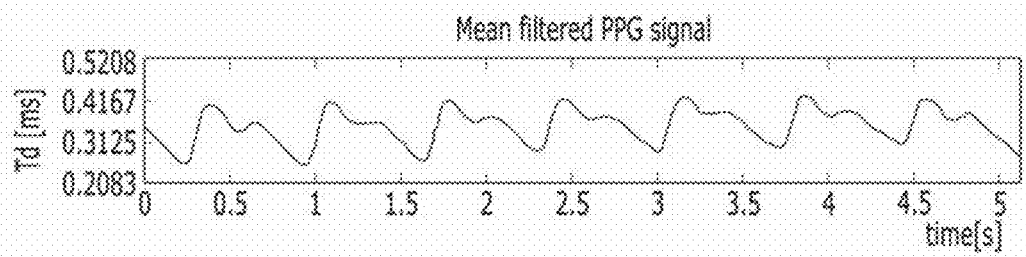
FIGS. 10A and 10B are a graph for a result measured by a photo plethysmography of a wearable terminal according to one embodiment of the present invention.
Figure 10B:
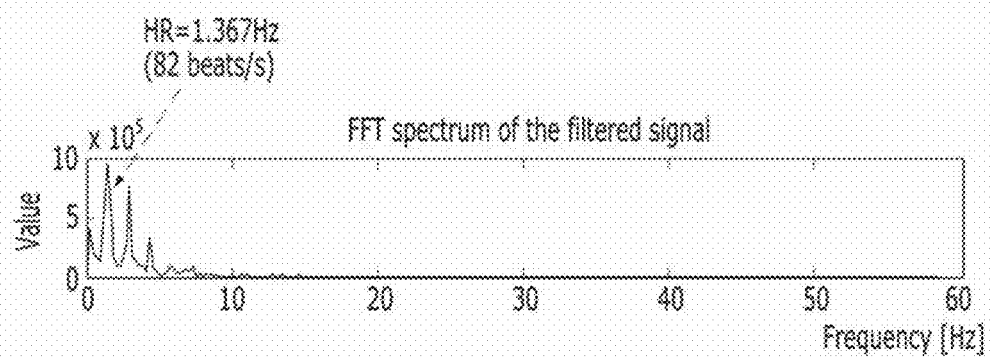

FIG. 10 is a graph for a result measured by a photo plethysmography 200 of a wearable terminal 100 according to one embodiment of the present invention. FIG. 10 A indicates strength of a reflection signal from which a noise of FIG. 9 A is eliminated.

If an acceleration sensor 143 measures a movement and detects shaking, a noise can be eliminated in a manner of getting rid of a change corresponding to a cycle corresponding to the shaking. If a result of FIG. 10 A is converted into a graph for a frequency using FFT (Fast-Fourier Transform), as shown in FIG. 10 B, a big signal size is calculated on 1.367 Hz (=82 beats/s). Hence, it is able to accurately measure a heart rate.

As mentioned in the foregoing description, in case of filtering a noise using an acceleration sensor 143, since an error resulted from running or exercising is able to be reduced, a user can obtain an accurate heart rate information while exercising.

Figure 11:
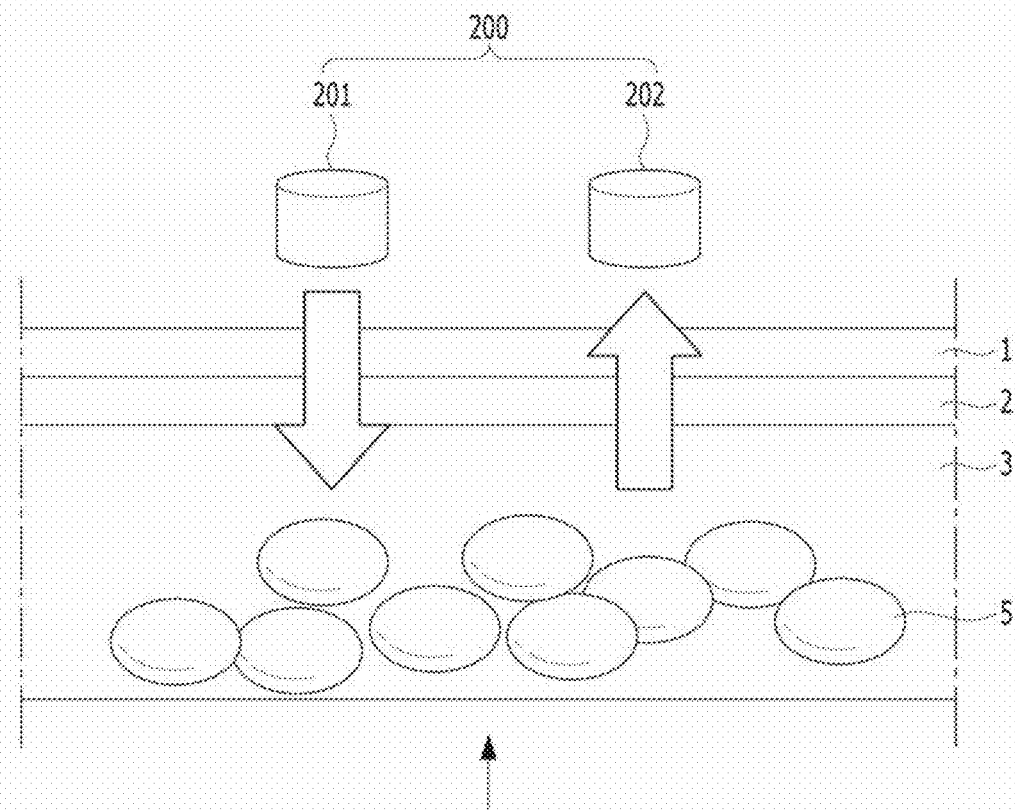
FIG. 11 is a diagram for explaining an operation of a photo plethysmography according to a movement of a wearable terminal moving to a direction opposite to a direction of the wearable terminal according to one embodiment of the present invention.
Figure 12:
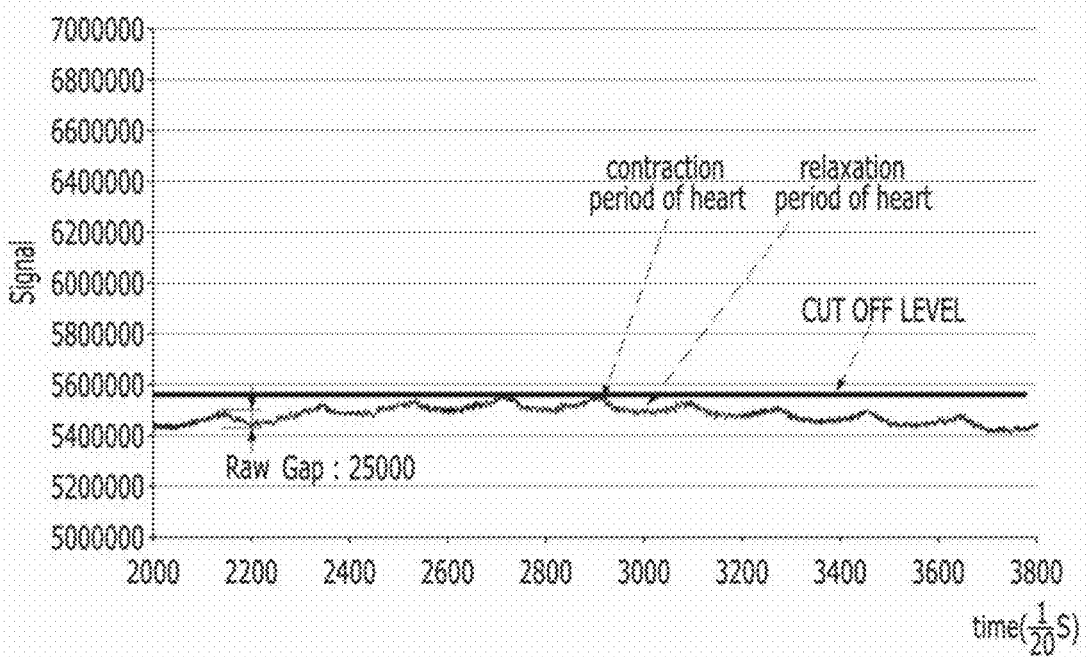
FIG. 12 is a graph showing a measurement result of FIG. 11.

Besides a movement moving with a prescribed cycle as a pattern such as running or walking, strength of a reflection signal may vary due to a consistently occurring movement. FIG. 11 is a diagram for explaining an operation of a photo plethysmography 200 according to a movement of a wearable terminal 100 moving to a direction opposite to a direction of the wearable terminal according to one embodiment of the present invention and FIG. 12 is a graph showing a measurement result of FIG. 11.

Referring to FIG. 11, if the wearable terminal 100 and a body of a user move to a direction (up direction in the drawing) opposite to a direction at which the photo plethysmography 200 of a main body is positioned, a blood cell 5 in a blood vessel 3 moves to a direction separated from the photo plethysmography 200. In particular, as a distance between the photo plethysmography 200 and the blood cell 5 is getting far, a size of a reflection signal detected by a receiver 202 is reduced compared to a size of a output signal shot from a transmitter 201.

As a size of a total signal is getting smaller, a difference (raw gap) between strength of a reflection signal shown in a contraction period of a heart and strength of a reflection signal shown in a relaxation period of the heart is getting smaller as well. Hence, it is difficult to measure an accurate cycle. In this case, if the size of the reflection signal is amplified, the difference between the strength of the reflection signal shown in the contraction period and the strength of the reflection signal shown in the relaxation period of the heart is considerably amplified. By doing so, it is able to accurately measure a heart rate.

Figure 13:
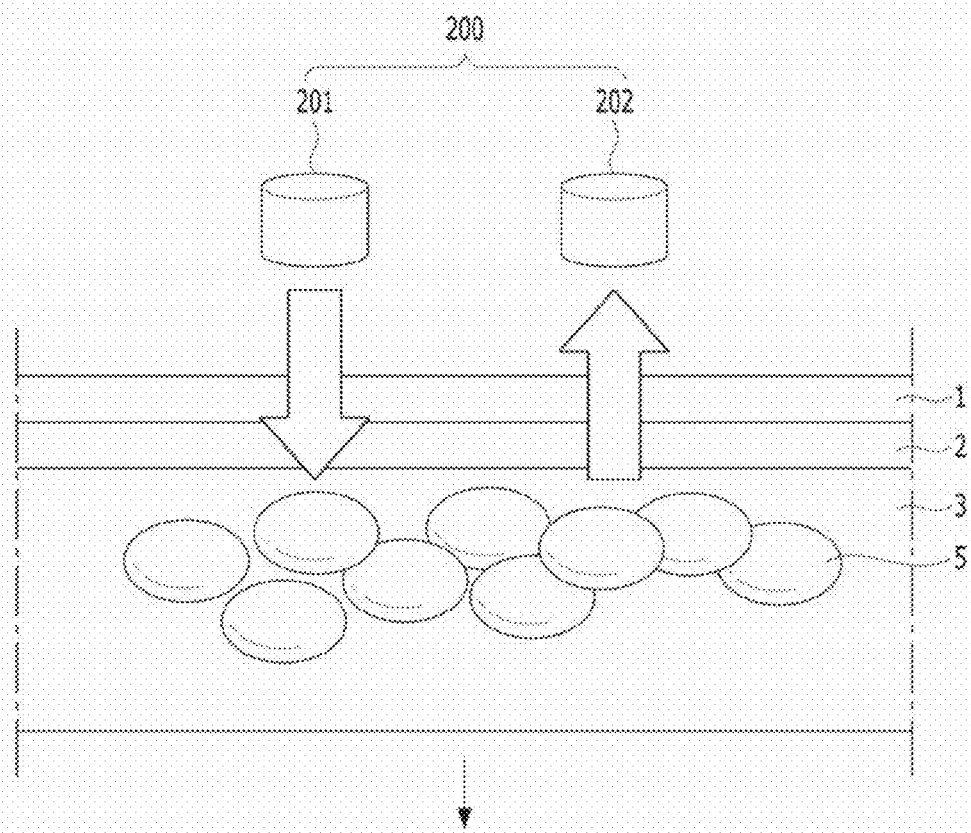
FIG. 13 is a diagram for explaining an operation of a photo plethysmography according to a movement of a wearable terminal moving to a direction identical to a direction of the wearable terminal according to one embodiment of the present invention.
Figure 14:
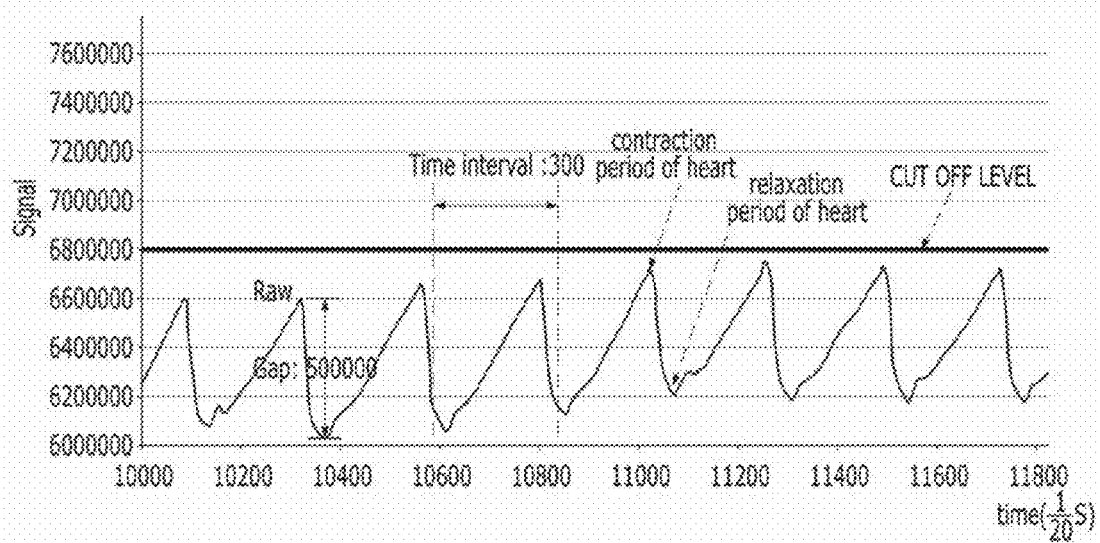
FIG. 14 is a graph for a measurement result of FIG. 13.

FIG. 13 is a diagram for explaining an operation of a photo plethysmography 200 according to a movement of a wearable terminal 100 moving to a direction identical to a direction of the wearable terminal according to one embodiment of the present invention and FIG. 14 is a graph for a measurement result of FIG. 13.

Referring to FIG. 13, if a user moves to a direction (down direction in the drawing) at which the photo plethysmography 200 is positioned, a blood cell 5 moves to a direction getting close to the photo plethysmography 200. If the blood cell 5 is cornered to the direction getting close to the photo plethysmography 200, strength of a reflection signal becomes stronger compared to strength of a output signal. As shown in FIG. 14, a big value is derived.

In particular, a difference (raw gap) between a contraction period of a heart and a relaxation period of the heart becomes big. Compared to a case that the user moves to a direction opposite to a direction at which the photo plethysmography 200 is positioned, the difference may become about 20 times bigger. If the contraction period of the heart and the relaxation period of the heart become clear, an accurate heart rate can be obtained.

And, an abnormal signal cut-off level can be adjusted. An abnormal signal indicates an abnormally big reflection signal. The abnormal signal can be considered as a noise. The abnormal signal cut-off level means a level used for eliminating the abnormal signal.

As shown in FIG. 12, if strength of a reflection signal is weak, the abnormal signal cut-off level should be lowered to eliminate a noise. On the contrary, as shown in FIG. 14, when strength of a reflection signal is strong, if the abnormal signal cur-off level is set too low, a normal signal may also be eliminated as well as a noise.

Hence, if an acceleration sensor 143 detects that the wearable terminal 100 is moving to an opposite direction, it may lower the abnormal signal cut-off level (refer to FIG. 12). On the contrary, if the acceleration sensor 143 detects that the wearable terminal 100 is moving to an identical direction, it may higher the abnormal signal cut-off level (refer to FIG. 14).

Figure 15:
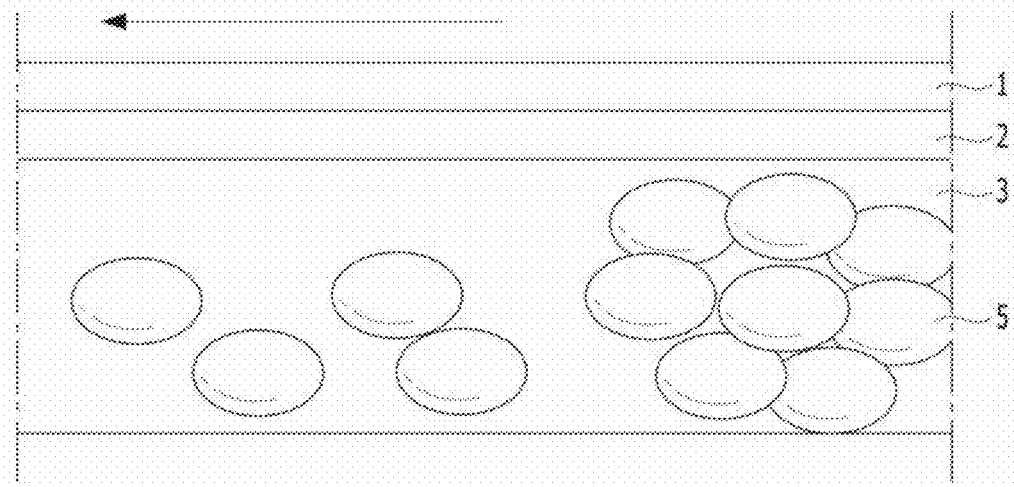
FIG. 15 is a diagram for explaining an operation of a photo plethysmography according to a movement of a wearable terminal moving to a direction different from a direction of a blood flow according to one embodiment of the present invention.
Figure 16:
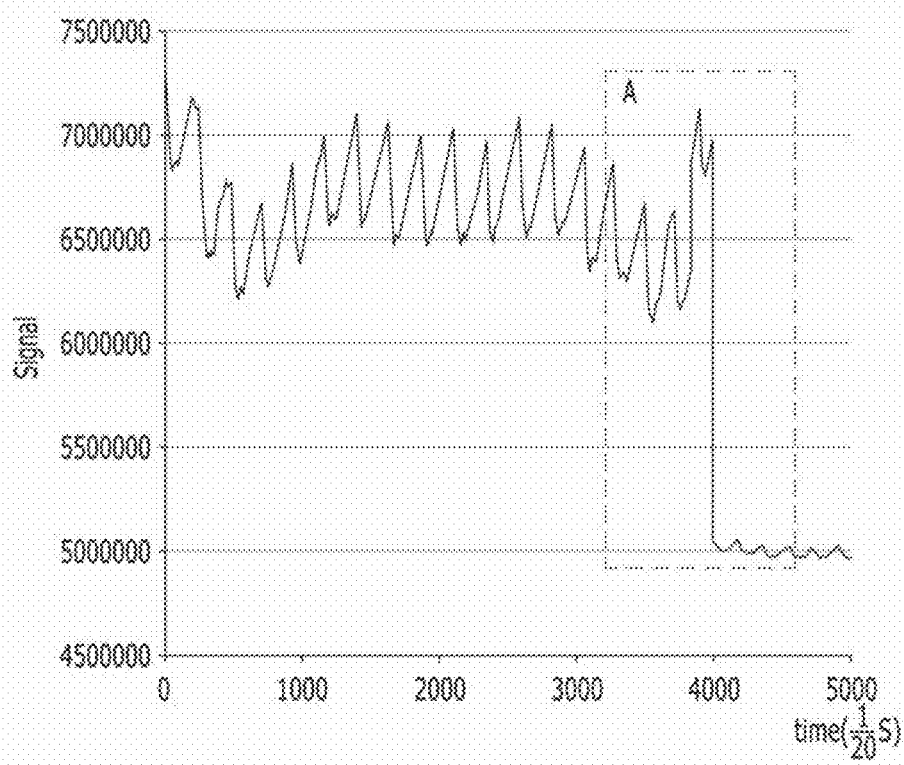
FIG. 16 is a graph for a measurement result of FIG. 15.

FIG. 15 is a diagram for explaining an operation of a photo plethysmography 200 according to a movement of a wearable terminal 100 moving to a direction different from a direction of a blood flow according to one embodiment of the present invention and FIG. 16 is a graph for a measurement result of FIG. 15.

In the drawing, when it is assumed that a blood flow flows in the left direction, if the wearable terminal moves to a direction opposite to the direction of the blood flow, as shown in FIG. 15, a blood cell 5 is cornered to the left direction. Although strength of a reflection signal becomes strong in a moment due to the blood cell 5 cornered into the left, if a less amount of blood cell 5 in the right arrives at the bottom of the photo plethysmography 200, as shown in FIG. 16 A, the strength of the reflection signal rapidly becomes weak.

Similar to the graph shown in FIG. 12, since strength of a reference signal becomes weak in the A of FIG. 16, a controller performs a compensation control for the change to obtain an accurate heart rate data. The controller amplifies the rapidly reduced strength of the reflection signal and lowers an abnormal signal cut-off level to offset the change of the strength of the reflection signal due to the movement of the wearable terminal and may be able to obtain a result similar to a result of which the wearable terminal is not moved.

Figure 17:
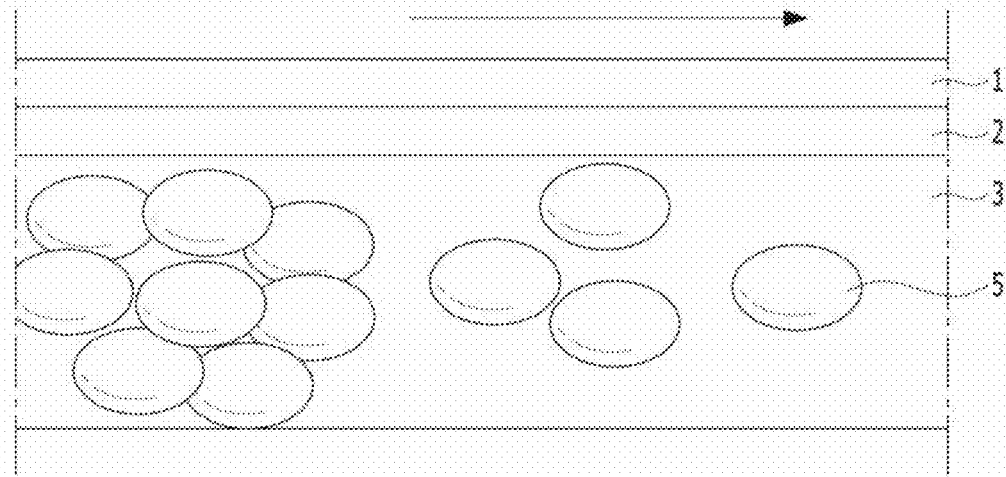
FIG. 17 is a diagram for explaining an operation of a photo plethysmography according to a movement of a wearable terminal moving to an direction identical to a direction of a blood flow according to one embodiment of the present invention.
Figure 18:
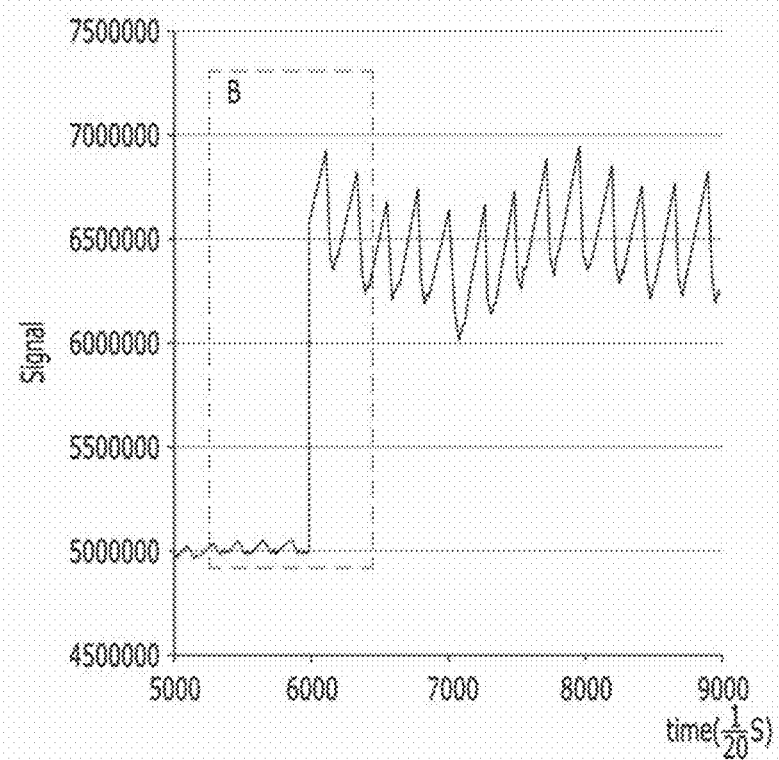
FIG. 18 is a graph for a measurement result of FIG. 17.

FIG. 17 is a diagram for explaining an operation of a photo plethysmography 200 according to a movement of a wearable terminal 100 moving to a direction identical to a direction of a blood flow according to one embodiment of the present invention and FIG. 18 is a graph for a measurement result of FIG. 17.

In the drawing, if the wearable terminal 100 and a body of a user move to a direction identical to a direction of a blood flow, strength of a reflection signal is weak at first due to a less amount of a blood cell 5. Yet, if the blood cell 5 cornered to the right arrives at the bottom of the photo plethysmography 200 according to the blood flow, as show in B of FIG. 17, the strength of the reflection signal rapidly becomes strong.

Similar to FIG. 14, since strength of a reference signal becomes strong in the B of FIG. 17, a controller performs a compensation control for the change to obtain an accurate heart rate data. The controller decreases the rapidly strengthened strength of the reflection signal and raises an abnormal signal cut-off level to offset the change of the strength of the reflection signal received in the photo plethysmography 200 due to the movement of the wearable terminal and may be able to obtain a result similar to a result of which the wearable terminal is not moved.

Since a movement of the wearable terminal is detected by an acceleration sensor 143 and a strength change of a reflection signal according to the movement of the wearable terminal can be offset, a more accurate heart rate data can be obtained in a manner of eliminating an error occurred due to the movement from the reflection signal.

In particular, it was difficult for a user to measure a heart rate using a legacy photo plethysmography 200 while the user is moving. On the contrary, a photo plethysmography 200 according to the present invention is able to measure a heart rate while the user is exercising. Hence, the user can consistently monitor the heart rate by measuring changing heart rate in case of exercising. For a person who has a weak heart, the wearable terminal 100 according to the present invention is able to guide the person to exercise in a level without damaging the heart.

Figure 19:
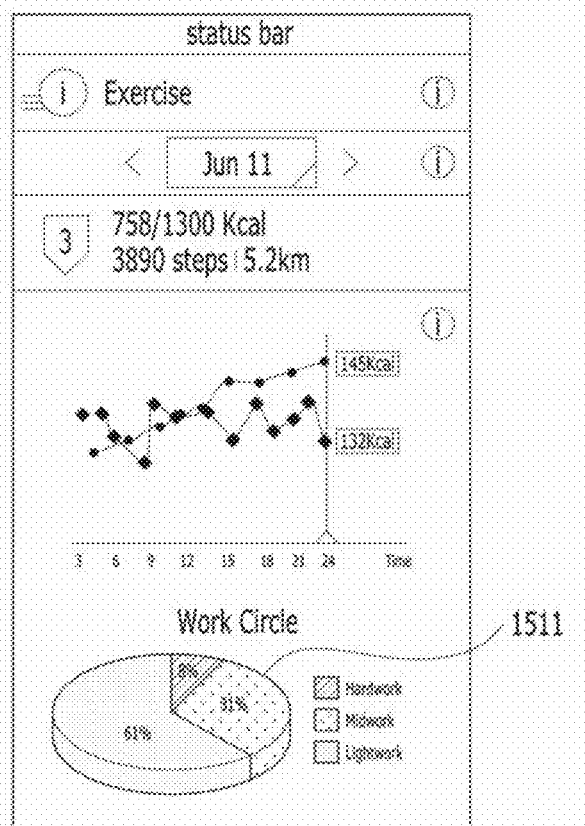
FIG. 19 is a diagram for a screen of a wearable terminal according to the present invention on which a calculated calorie consumption is displayed.

And, an application and the like of the wearable terminal 100 can calculate calorie based on a heart rate measured by the photo plethysmography 200. FIG. 19 is a diagram for a screen of the wearable terminal 100 according to the present invention on which a calculated calorie consumption is displayed.

An acceleration sensor 143 measures a movement of a user in a manner of detecting a change of acceleration. When a user is walking, the wearable terminal 100 is moving in an up and down direction. Hence, the acceleration sensor can measure a step count by measuring acceleration change in a walking motion. Hence, the wearable terminal can calculate a calorie consumption compared to a regular step count.

Since a calorie consumption varies according to a speed or a weight of a user in an identical step count, a more accurate calorie can be calculated in a manner of adding weight information or using a speed which is calculated based on a moving distance measured by a GPS.

Yet, although the acceleration sensor 143 is able to detect an acceleration change of the wearable terminal 100, a calculated calorie may not be accurate since a user may not be in a state of exercising.

Figure 20A:
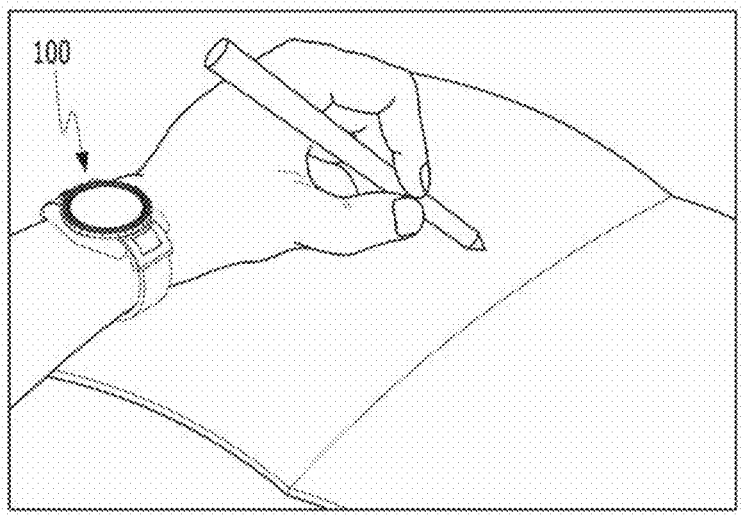
FIGS. 20A, 20B, 21A, and 21B are diagrams for measurement results of an acceleration sensor and a photo plethysmography according to a movement of a user.
Figure 20B:
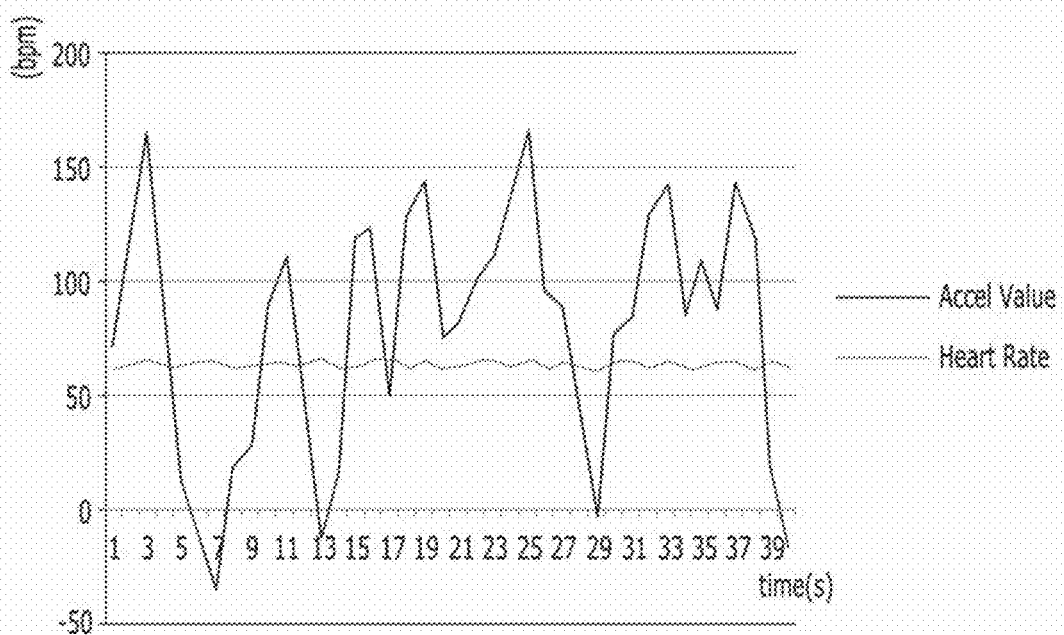
Figure 21A:
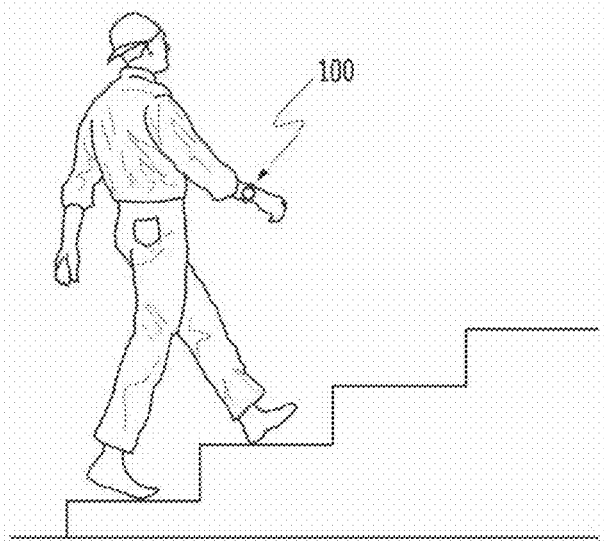
Figure 21B:
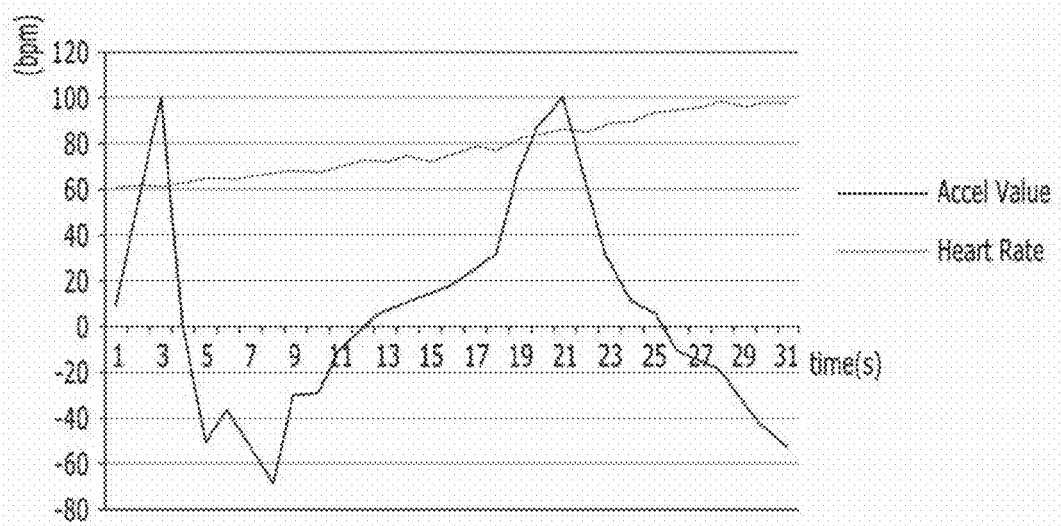

FIGS. 20 and 21 are diagrams for measurement results of an acceleration sensor 143 and a photo plethysmography 200 according to a movement of a user. As shown in FIG. 20, in case of writing letter while a watch-type wearable terminal 100 is worn on a wrist, although change of the acceleration sensor 143 is shown as big, a calorie consumption is low because the user is not exercising.

And, when a user is riding a horse or getting on a vehicle, shaking in up and down direction is detected. Hence, the shaking can be recognized as a step count. Yet, since it is not an exercise of the user, a calorie consumption is low.

As shown in FIG. 21, when a user is walking up the steps, a calorie consumption is high because it forms a better exercise compared to walking down plain. Yet, an acceleration sensor 143 may measure a movement of walking up the step as same as a movement of walking down plains.

In order to resolve errors shown in FIG. 20 and FIG. 21, if an exercise intensity is high, a calorie consumption is raised on the basis of a calorie (reference calorie consumption) consumed in walking down plains with a reference speed. If the exercise intensity is low, the calorie consumption can be lowered. By doing so, a precise calorie can be calculated.

If a heart rate is fast, it may indicate that a user is doing an exercise of a high level. If the heart rate is slow, it may indicate that the user is doing an exercise of a low level. Hence, an intensity of an actual exercise can be measured using a heart rate. Hence, as shown in FIG. 20 B, if there is little change of a heart rate while an amount of change of the acceleration sensor 143 is big, it may be identified as the intensity of the exercise is low (low level) and a calorie consumption can be calculated as low.

On the contrary, as shown in FIG. 21 B, if there is an acceleration change while a heart rate is increasing, a calorie can be calculated under an assumption that a user is actually doing an exercise. If a heart rate is greater than a heart rate (reference heart rate) of doing an exercise of walking down in plains with a reference speed, it may be determined as a user is doing an exercise of a high level. If a heart rate is identical to the reference heart rate, it may be determined as a user is doing an exercise of a middle level. If a heart rate is less than the reference heart rate, it may be determined as a user is doing an exercise of a low level.

In case that a user is walking up the steps, a change of a heart rate is bigger compared to a case of walking down plains. Hence, a calorie consumption can be calculated under an assumption that calorie is more consumed compared to a case of walking down plains.

A method of determining an intensity of exercise using a heart rate and calculating calorie based on the determined intensity of exercise can be more accurate than a method of calculating calorie based on an acceleration change measured by the acceleration sensor 143 only.

And, as shown in FIG. 19, the wearable terminal may provide a user with a graph showing intensity of a daily movement to inform the user of whether an exercise is sufficient or deficient in a manner of consistently detecting the movement of the user. The wearable terminal detects an amount of exercise and the user may be able to know whether the amount of exercise is sufficient or deficient.

Figure 22:
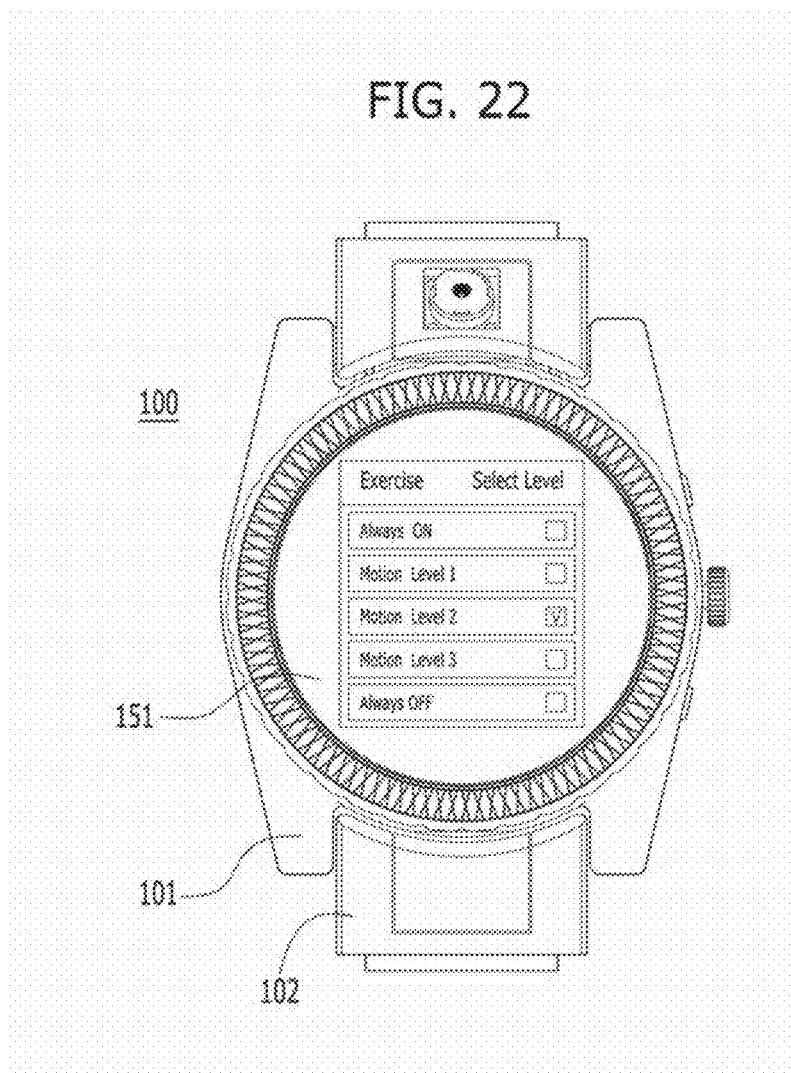
FIG. 22 is a diagram for a setting screen of a photo plethysmography according to one embodiment of the present invention.

FIG. 22 is a diagram for a setting screen of a photo plethysmography 200 according to one embodiment of the present invention. In case of consistently driving the photo plethysmography 200, power of the wearable terminal 100 is consumed a lot. When it is necessary to consistently drive the photo plethysmography 200, the photo plethysmography 200 can be controlled to be consistently driven by checking a state of 'always on'. The photo plethysmography 200 can be used only when a user is doing an exercise. Or, the photo plethysmography 200 can be used to prevent a heart rate from being increased in an intense movement.

As shown in FIG. 22, the photo plethysmography 200 can be configured to be driven only when a movement of an intensity greater than a specific intensity is detected in a manner of classifying the intensity of the movement to drive the photo plethysmography 200. And, the photo plethysmography 200 can be activated all the time or can be turned off all the time.

Figure 23A:
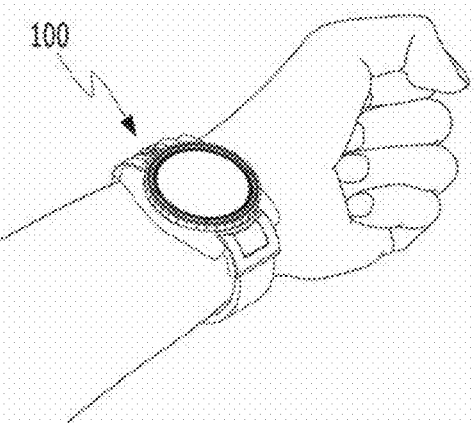
FIGS. 23A to 23C are a diagram for an example of wearing a photo plethysmography according to one embodiment of the present invention.
Figure 23B:
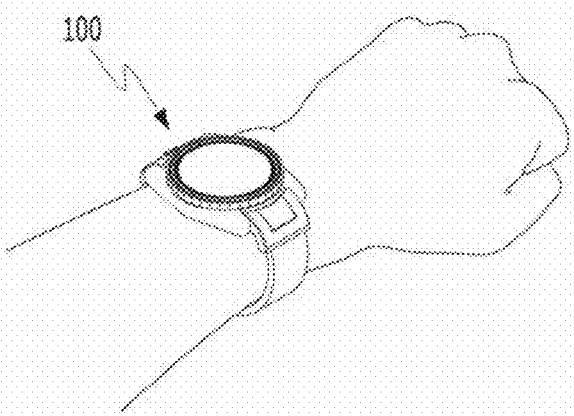
Figure 23C:
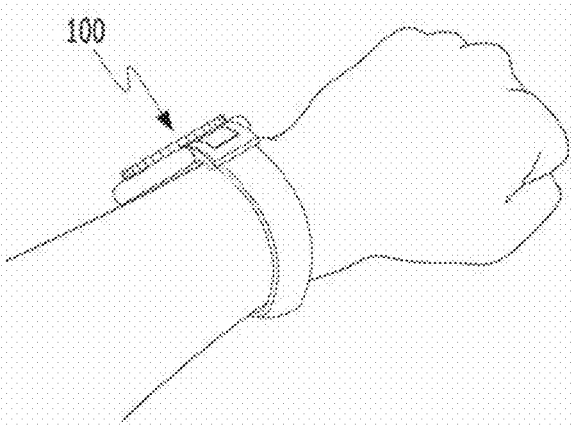

FIG. 23 is a diagram for an example of wearing a photo plethysmography 200 according to one embodiment of the present invention. If the photo plethysmography 200 detects a heart rate, it may indicate that a user is wearing the photo plethysmography 200. In case of using the photo plethysmography 200, a strength difference of a reflection signal may be different from each other depending on a distribution of blood vessel 3. Hence, a state (direction) of being worn on a wrist of a user of the photo plethysmography 200 can be identified according to strength of a heart rate. As shown in FIG. 23 A, if the wearable terminal 100 is worn on the inside of the wrist, the strength of the reflection signal becomes too strong since a lot of blood vessels are passing through and there may occur time difference in terms of increase and decrease of an amount of blood in every blood vessel 3. Hence, an error may occur when a heart rate is calculated.

As shown in FIG. 23 C, if the wearable terminal 100 is worn on a side of the wrist, it may be difficult to measure an accurate heart rate since the wearable terminal is too much separated from the blood vessel 3. As shown in FIG. 23 B, if the wearable terminal 100 is worn on the outside of the wrist, an accurate heart rate can be measured. Hence, it is necessary to guide a user to wear the wearable terminal 100 on a correct position.

In the following description, although the present specification is explained based on a mobile terminal of a watch-type, the present invention can also be applied to other wearable terminals 100. The controller detects strength of a reflection signal received by the photo plethysmography 200. If the strength of the reflection signal is weak, the controller can guide a user to wear the wearable terminal on a correct position. In order to guide a wearing position of the wearable terminal 100, various signal indicators can be provided on the display unit 151.

Figure 24:
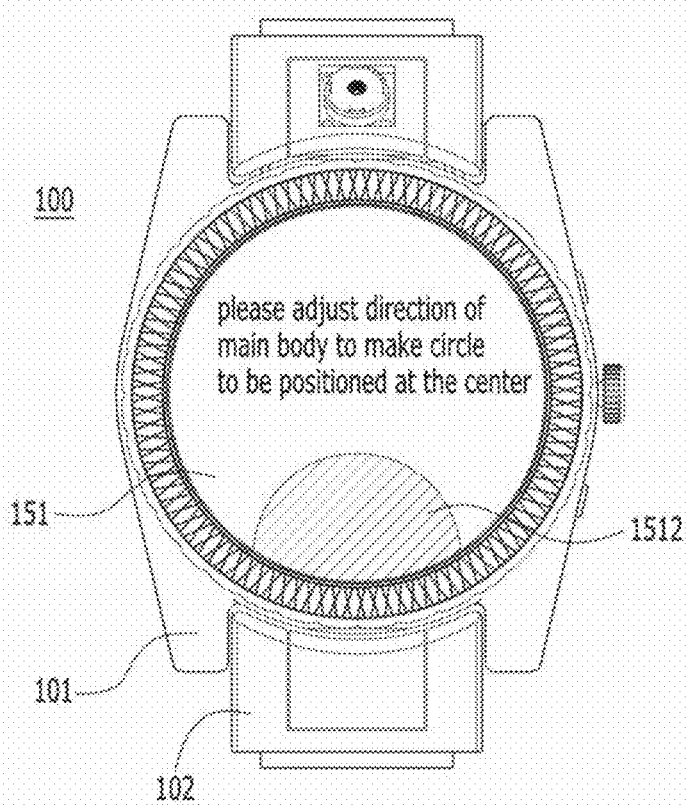
FIGS. 24 to 31 are diagrams for various embodiments of a screen configured to guide a wearing position of a wearable terminal according to the present invention.

FIGS. 24 to 31 are diagrams for various embodiments of a screen configured to guide a wearing position of a wearable terminal 100 according to the present invention. Referring to FIG. 24, a signal indicator 1512 is displayed on a screen of the display unit 151 and a user controls a position of the wearable terminal 100 to make the signal indicator 1512 to be positioned at the center of the screen.

In the drawing, since a circle is positioned at the bottom of the display unit, if the wearable terminal 100 is moved to a down direction, the circle 1512 is positioned at the center of the display unit 151. In order to guide a user to move in a direction orthogonal to a band 102 except a movement moving in an extended direction of the band 102, the circle may be positioned at the left side or the right side.

Figure 25:
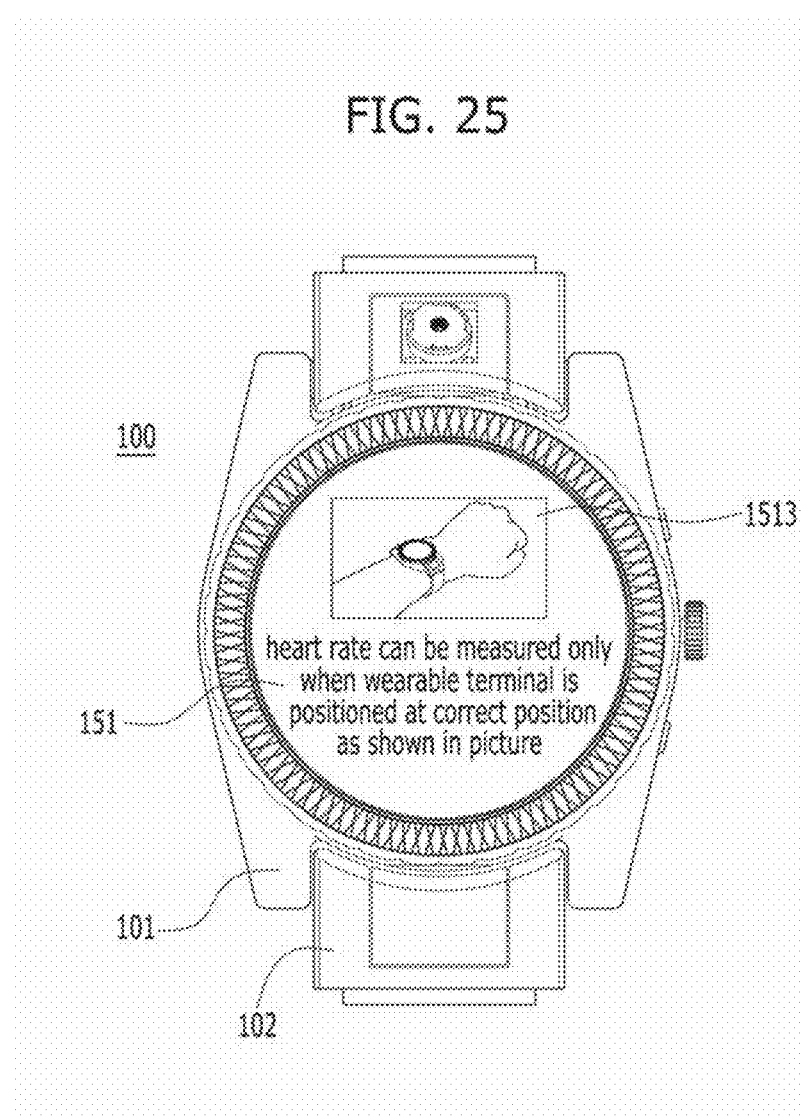
Figure 26:
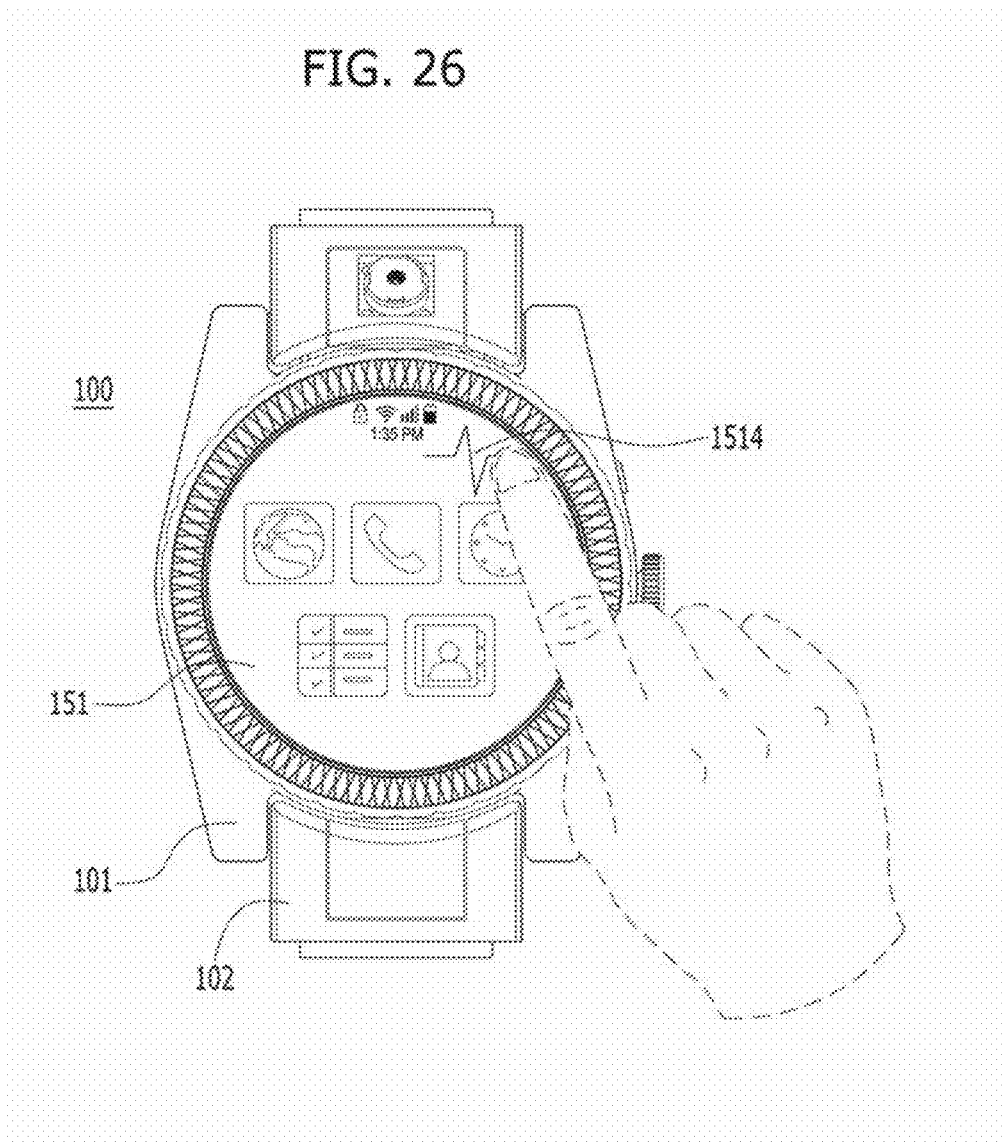

As shown in FIG. 25, a signal indicator 1513 can guide a user to wear the wearable terminal 100 on a correct position in a manner of providing an image or a picture showing a correct wearing state to the user.

In case that it is difficult to accurately measure a heart rate since a reflection signal is too weak, as shown in FIG. 26 to FIG. 31, a signal indicator 1514, which is positioned at one side of a screen, may inform a user that a position of the wearable terminal 100 needs to be adjusted again.

Figure 27:
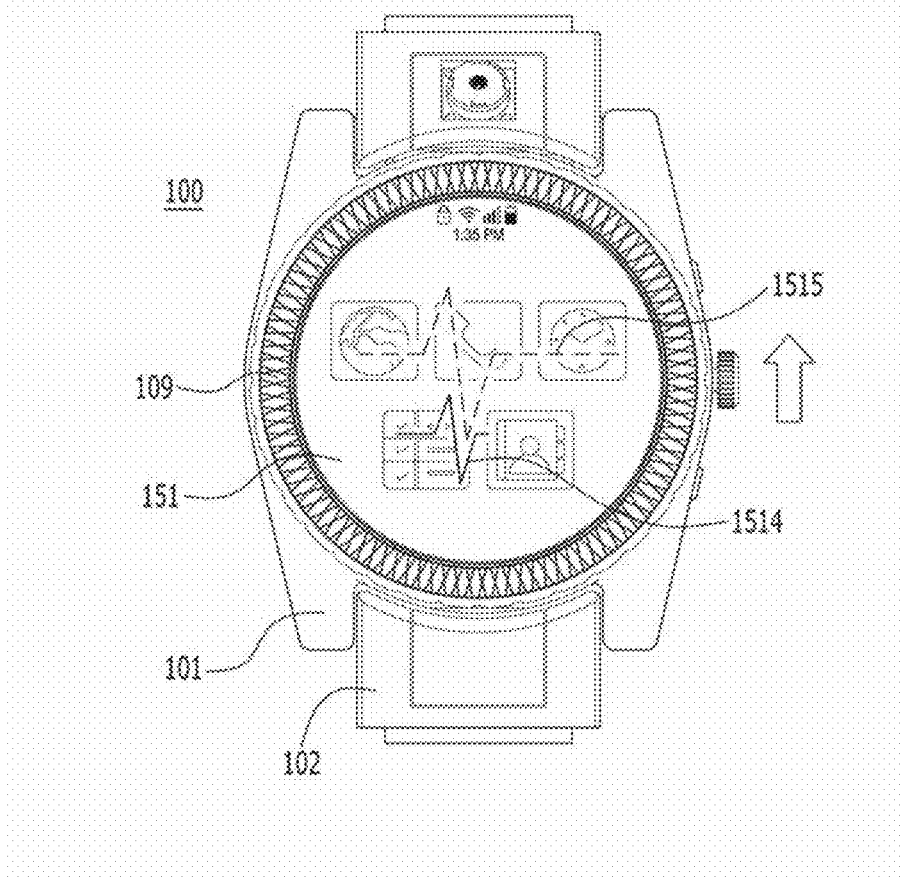
Figure 28:
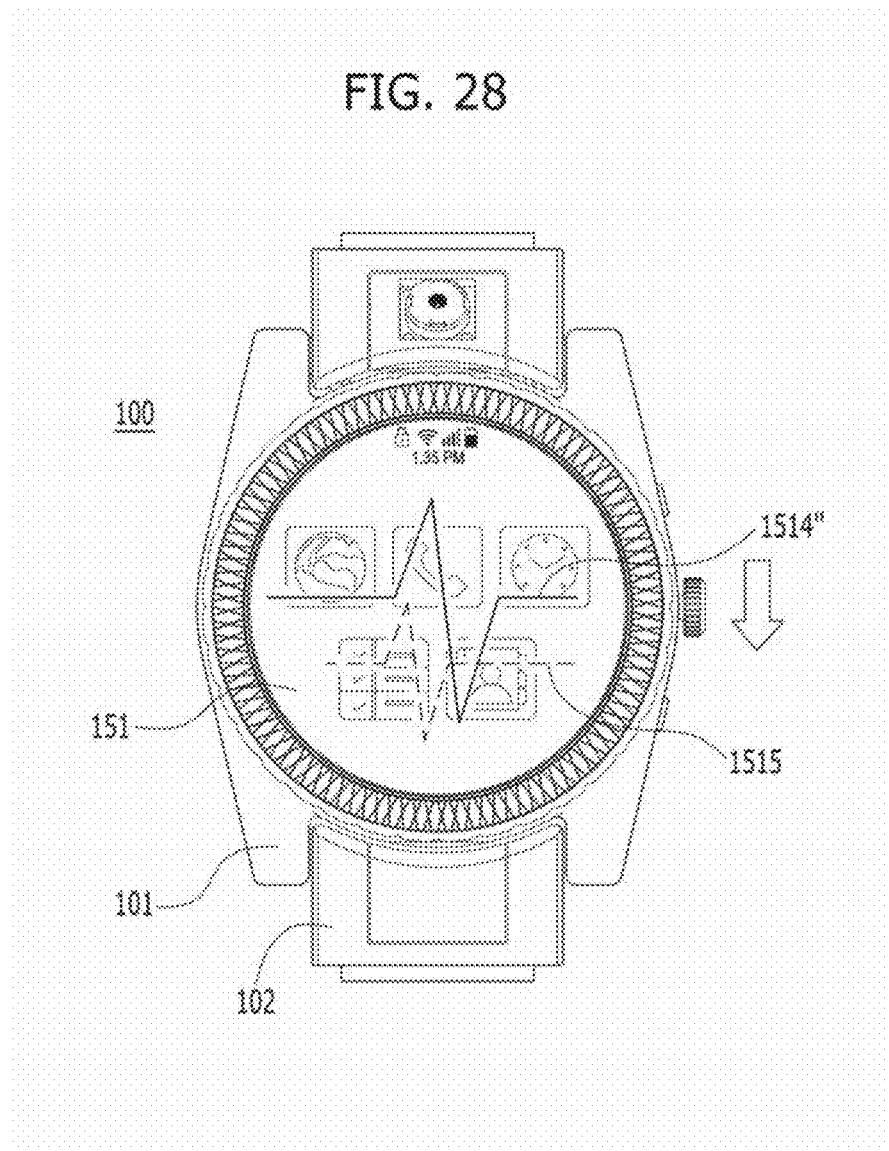

If the user touches and selects the signal indicator 1514, as shown in FIG. 27 or FIG. 28, the signal indicator 1514 and a reference indicator 1515 are displayed on the screen. Although FIG. 27 and FIG. 28 show that the signal indicator 1514 and the reference indicator 1515 are enlarged to a size as large as a whole screen, the signal indicator 1514 and the reference indicator 1515 can be positioned at one side of the screen or can be outputted in a manner of being overlapped with a previously outputted screen.

The signal indicator 1514 and the reference indicator 1515 are not matched with each other in size and position. If the signal indicator 1514 is smaller than the reference indicator 1515 (FIG. 27), it indicates a case that strength of a signal is weaker than strength of a required reflection signal (valid signal strength). On the contrary, if the signal indicator 1514 is larger than the reference indicator 1515 (FIG. 28), it indicates a case that strength of a signal is stronger than strength of a valid signal.

Figure 29:
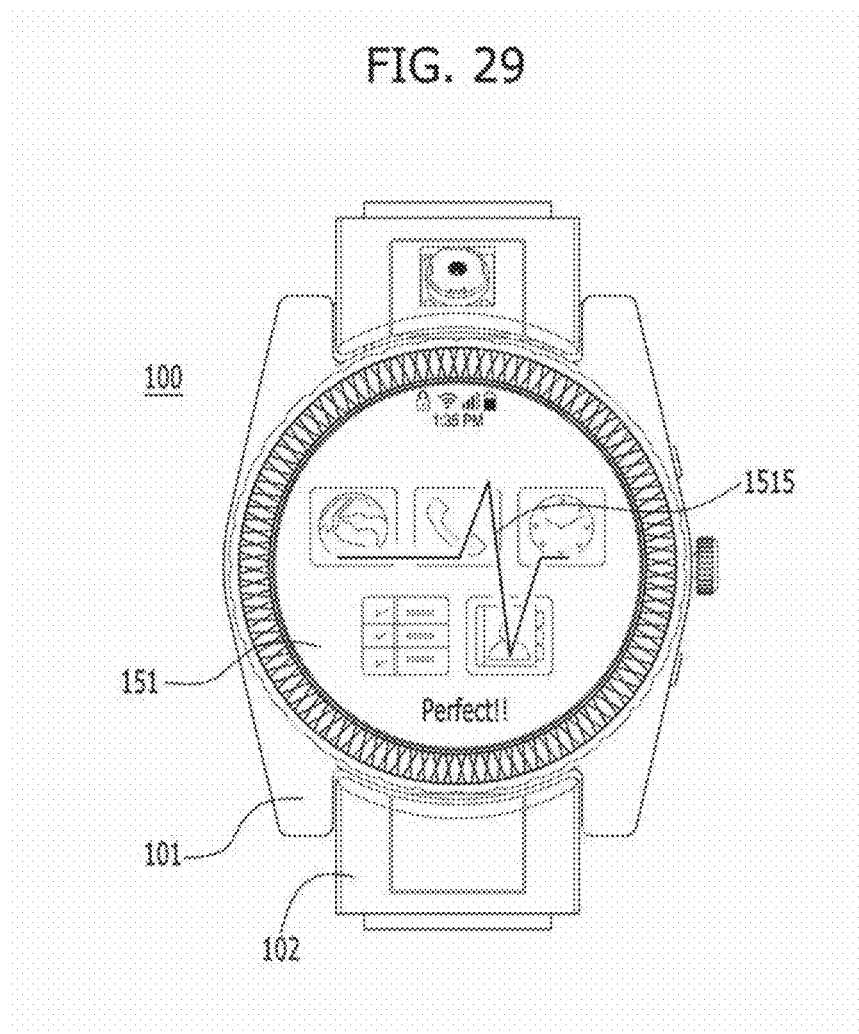

Referring to FIG. 27, since strength of a signal is weaker than strength of a valid signal, it indicates a state of being worn of the wearable terminal 100 shown in FIG. 23 C. Referring to FIG. 28, since strength of a signal is stronger than strength of a valid signal, it indicates a state of being worn of the wearable terminal 100 shown in FIG. 23 A. If the wearable terminal 100 is moved to make the reference indicator 1515 to be matched with the signal indicator, as shown in FIG. 29, the wearable terminal is positioned at a correct positioned and a guide used for wearing the wearable terminal on the correct position is terminated.

Figure 30:
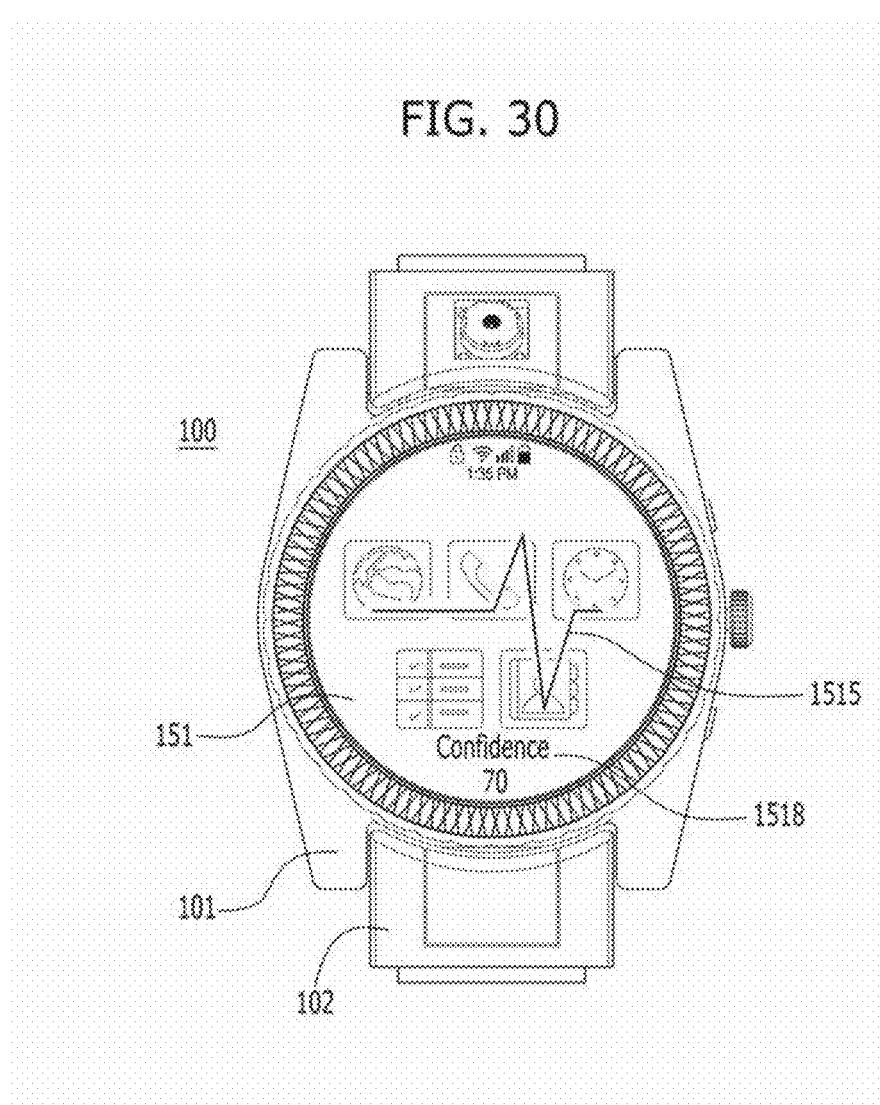
Figure 31:
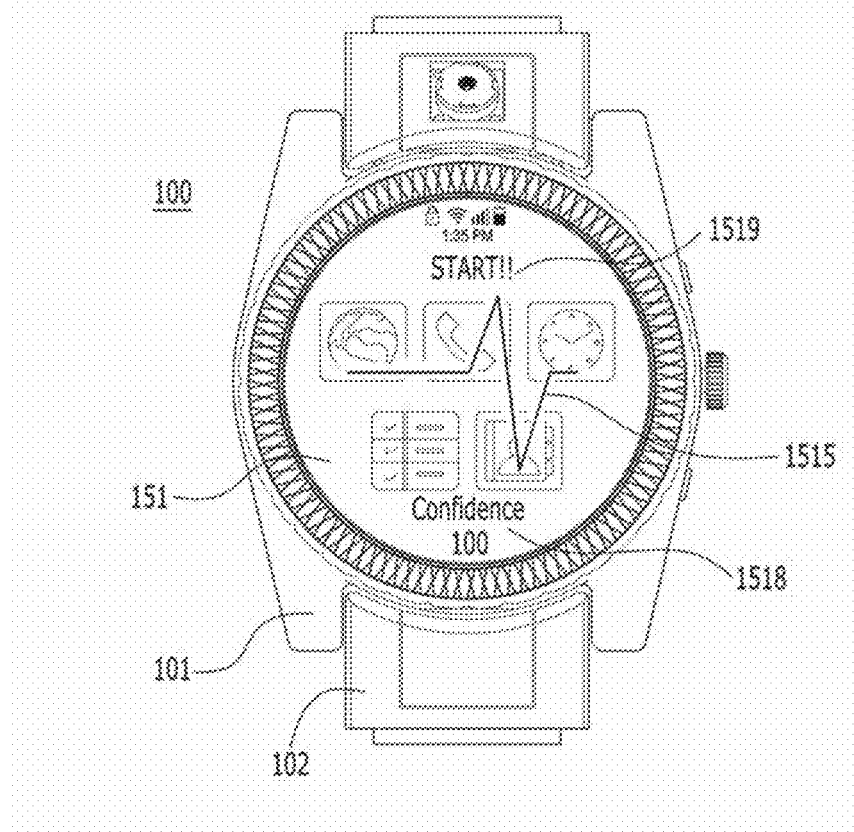

In case of resetting a position, it is necessary to have time to check whether the position corresponds to a correct position. In this case, it may make the signal indicator 1514 blink. As shown in FIG. 30, a confidence level can be represented by a number 1518. If the confidence level becomes 100%, blink of the signal indicator is stopped and driving of the photo plethysmography 200 starts. Or, as shown in FIG. 31, the confidence level 1518 is displayed on the screen and the wearable terminal informs 1519 a user of the driving of the photo plethysmography 200.

As mentioned in the foregoing description, according to at least one embodiment of the present invention, in case of measuring a pulse wave using a photo plethysmography 200, the present invention can provide a wearable terminal 100 capable of eliminating a noise occurred according to a movement and obtaining an accurate heart rate.

And, an accurate heart rate can be obtained by eliminating an error occurred according to a wearing position of a wearable terminal in a manner of guiding the wearing position of the wearable terminal 100.

And, a more accurate calorie consumption can be measured using a heart rate and an acceleration sensor 143.

The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:
1. A wearable terminal, comprising:
a main body comprising a side configured to contact a body part of a user;
a photo plethysmography located at the side of the main body and comprising:
a transmitter configured to output a signal; and
a receiver configured to detect a reflection signal that is reflection of the output signal;
a cover of the main body configured to cover the photo plethysmography, the cover comprising:

transparent units aligned with the transmitter and the receiver, the transparent units configured to pass the output signal and the reflection signal; and a barrier unit positioned between the transparent units and configured to shield the output signal and the reflection signal;

a rubber located between the cover and the photo plethysmography, the rubber including openings that are aligned with the transparent units, and at least one of the openings also aligned with the transmitter and at least one of the openings also aligned with the receiver such that the rubber is configured to block the signal output from the transmitter directly flowing into the receiver; and a controller configured to measure a heart rate of the user based on the detected reflection signal.

2. The wearable terminal of claim 1, wherein the cover is adhered to the main body via waterproof tape.

3. The wearable terminal of claim 1, wherein the transmitter comprises a green light-emitting diode (LED) configured to output green light as the output signal.

4. A wearable terminal, comprising:
a main body comprising a first side configured to contact a body part of a user when the wearable terminal is worn by the user and a second side that is an opposite side of the first side;
a photo plethysmography located at the first side of the main body and comprising:
  a transmitter configured to output a signal, and
  a receiver configured to detect a reflection signal that is a reflection of the output signal from a blood cell in a blood vessel of the user;
an acceleration sensor configured to detect movement of the main body when the wearable terminal moves in a first direction toward a direction that the first side faces or in a second direction toward a direction that the second side faces according to movement of the body part, the second direction being an opposite direction of the first direction; and
a controller configured to:
  reduce a first size of the detected reflection signal in response to detection, by the acceleration sensor, of the movement of the main body in the first direction;
  amplify a second size of the detected reflection signal in response to detection, by the acceleration sensor, of the movement of the main body in the second direction;
  calculate reflection signal data based on the first or second direction and a speed of the movement detected by the acceleration sensor by compensating the reflection signal; and
  calculate a heart rate of the user based on a number of changes in the reflection signal data per reference time.

5. The wearable terminal of claim 4, wherein the controller is further configured to eliminate a change of the reflection signal having an interval in response to detection of the movement of the main body having a prescribed cycle such that the interval corresponds to the prescribed cycle.

6. The wearable terminal of claim 4, wherein the first size of the detected reflection signal is greater than the second size of the detected reflection signal.

7. The wearable terminal of claim 4, wherein the controller is further configured to:
calculate the reflection signal data by eliminating a reflection signal that is higher than an abnormal signal cut-off level;
lower the abnormal signal cut-off level in response to detection of the movement of the main body in the second direction; and
raise the abnormal signal cut-off level in response to detection of the movement of the main body in the first direction.

8. The wearable terminal of claim 4, wherein the controller is further configured to:
increase a measurement value of the reflection signal in response to detection of the movement of the main body in a direction that is opposite to a moving direction of the blood cell; and
decrease the measurement value of the reflection signal in response to detection of the movement of the main body in a direction that is the same as the moving direction of the blood cell.

9. The wearable terminal of claim 4, wherein the controller is further configured to:
cause the acceleration sensor to measure a step count of the user;
calculate calorie consumption corresponding to the measured step count; and
increase the calorie consumption when the calculated heart rate is greater than a reference heart rate; and
decrease the calorie consumption when the calculated heart rate is lower than the reference heart rate.

10. The wearable terminal of claim 9, further comprising a location information module configured to transceive location information of the user and determine a location change, wherein the controller is further configured to:
calculate a moving speed of the user based on the detected location change;
increase the calorie consumption when the moving speed is faster than a reference speed; and
decrease the calorie consumption when the moving speed is slower than the reference speed.

11. The wearable terminal of claim 4, wherein the controller is further configured to:
activate the photo plethysmography in response to detection of the movement of the main body that is greater than a reference distance; and
switch the photo plethysmography to an idle state in response to detection of the movement of the main body that is less than the reference distance.

12. The wearable terminal of claim 4, wherein the controller is further configured to cause the transmitter to increase strength of emitted light or shorten a cycle of light emission in response to detection of increased movement of the main body.

13. The wearable terminal of claim 4, wherein the controller is further configured to notify the user when a signal strength of the detected reflection signal measured by the photo plethysmography is out of a valid range.

14. The wearable terminal of claim 13, further comprising a display located on the second side of the main body, wherein the controller is further configured to cause the display to display a guide screen for guiding the user to change a position of the main body such that the first side of the main body contacts the body part in a correct configuration.

15. The wearable terminal of claim 14, wherein the guide screen comprises:
a signal indicator that increases in size as the measured signal strength increases and decreases in size when the signal strength decreases; and
a reference indicator configured to provide a reference for positioning the main body with respect to the body part such that the measured signal strength is within the valid range when the signal indicator substantially matches the reference indicator.

16. The wearable terminal of claim 14, wherein the controller is further configured to cause the display to display a confidence level indicator indicating the measured signal strength with respect to the valid range.

17. A method for controlling a wearable terminal comprising a main body, wherein the main body comprises a first side configured to contact a body part of a user when the wearable terminal is worn by the user and a second side that is an opposite side of the first side, the method comprising:
outputting a signal to the part of a user;
receiving a reflection signal that is a reflection of the output signal from a blood cell in a blood vessel of the user;
detecting movement of the main body when the wearable terminal moves in a first direction toward a direction that the first side faces or in a second direction toward a direction that the second side faces according to movement of the body part, the second direction being an opposite direction of the first direction;
reducing a size of the detected reflection signal in response to detection of the movement of the main body in the first direction;
amplifying a size of the detected reflection signal in response to detection of the movement of the main body in the second direction;
calculating reflection signal data based on the first or second direction and a speed of the detected movement by compensating the received reflection signal; and
calculating a heart rate of the user based on a number of changes in the reflection signal data per reference time.

18. The method of claim 17, wherein the calculating the heart rate comprises eliminating a change of the reflection signal having an interval in response to the detection of the movement having a prescribed cycle such that the interval corresponds to the prescribed cycle.

19. The method of claim 17, further comprising:
measuring a step count of the user based on the detected movement;
calculating calorie consumption corresponding to the step count;
increasing the calorie consumption when the calculated heart rate is greater than a reference heart rate; and
decreasing the calorie consumption when the calculated heart rate is lower than the reference heart rate.

* * * * *